(12) United States Patent
Anand et al.

(10) Patent No.: US 12,417,533 B2
(45) Date of Patent: *Sep. 16, 2025

(54) SYSTEMS AND METHODS FOR ARTIFICIAL INTELLIGENCE-BASED IMAGE ANALYSIS FOR CANCER ASSESSMENT

(71) Applicants: Progenics Pharmaceuticals, Inc., N. Billerica, MA (US); EXINI Diagnostics AB, Lund (SE)

(72) Inventors: Aseem Undvall Anand, Queens, NY (US); Karl Vilhelm Sjöstrand, Atlantic Highlands, NJ (US); Jens Filip Andreas Richter, Staffanstorp (SE)

(73) Assignees: Progenics Pharmaceuticals, Inc., N. Billerica, MA (US); EXINI Diagnostics AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/398,846

(22) Filed: Dec. 28, 2023

(65) Prior Publication Data
US 2024/0127437 A1    Apr. 18, 2024

Related U.S. Application Data

(63) Continuation of application No. 17/762,796, filed as application No. PCT/US2020/047500 on Aug. 21, (Continued)

(51) Int. Cl.
*G06V 10/25*   (2022.01)
*G06T 7/00*    (2017.01)
(Continued)

(52) U.S. Cl.
CPC ............ *G06T 7/0012* (2013.01); *G06V 10/25* (2022.01); *G16H 30/40* (2018.01); *G16H 50/20* (2018.01); *G06T 2207/10081* (2013.01)

(58) Field of Classification Search
CPC ......... G06T 7/0012; G06T 2207/10081; G06T 7/11; G06T 2207/10088;
(Continued)

(56) References Cited

U.S. PATENT DOCUMENTS

| 5,762,608 A | 6/1998 | Warne et al. |
| 6,944,330 B2 | 9/2005 | Novak et al. |

(Continued)

FOREIGN PATENT DOCUMENTS

| CN | 1200520 A | 12/1998 |
| CN | 1518719 A | 8/2004 |

(Continued)

OTHER PUBLICATIONS

Ali, A. et al., The Automated Bone Scan Index as a Predictor of Response to Prostate Radiotherapy in Men with Newly Diagnosed Metastatic Prostate Cancer: An Exploratory Analysis of STAMPEDE's "M1|RT Comparison", European Urology Oncology 3:412-419, (2020).

(Continued)

*Primary Examiner* — Phuoc Tran
(74) *Attorney, Agent, or Firm* — Choate, Hall & Stewart LLP; Ronen Adato

(57) ABSTRACT

Presented herein are systems and methods that provide for automated analysis of medical images to determine a predicted disease status (e.g., prostate cancer status) and/or a value corresponding to predicted risk of the disease status for a subject. The approaches described herein leverage artificial intelligence (AI) to analyze intensities of voxels in a functional image, such as a PET image, and determine a risk and/or likelihood that a subject's disease, e.g., cancer, is aggressive. The approaches described herein can provide predictions of whether a subject that presents a localized disease has and/or will develop aggressive disease, such as (Continued)

metastatic cancer. These predictions are generated in a fully automated fashion and can be used alone, or in combination with other cancer diagnostic metrics (e.g., to corroborate predictions and assessments or highlight potential errors). As such, they represent a valuable tool in support of improved cancer diagnosis and treatment.

20 Claims, 15 Drawing Sheets

Related U.S. Application Data 2020, now Pat. No. 11,900,597, which is a continuation-in-part of application No. 16/734,609, filed on Jan. 6, 2020, now Pat. No. 11,564,621.

(60) Provisional application No. 62/907,180, filed on Sep. 27, 2019.

(51) Int. Cl.
  *G16H 30/40* (2018.01)
  *G16H 50/20* (2018.01)

(58) Field of Classification Search
  CPC . G06T 2207/10104; G06T 2207/10108; G06T 2207/20081; G06T 2207/20084; G06T 2207/30081; G06V 10/25; G06V 10/82; G16H 30/40; G16H 50/20; G06N 3/0464
  See application file for complete search history.

(56) References Cited

U.S. PATENT DOCUMENTS

| | | |
|---|---|---|
| 7,450,747 B2 | 11/2008 | Jabri et al. |
| 7,751,605 B2 | 7/2010 | Gündel et al. |
| 7,876,938 B2 | 1/2011 | Huang et al. |
| 7,935,055 B2 | 5/2011 | Burckhardt |
| 7,970,194 B2 | 6/2011 | Kimura |
| 8,199,985 B2 | 6/2012 | Jakobsson et al. |
| 8,211,401 B2 | 7/2012 | Babich et al. |
| 8,467,856 B2 | 6/2013 | Renisch et al. |
| 8,538,166 B2 | 9/2013 | Gordon et al. |
| 8,606,349 B2 | 12/2013 | Rousso et al. |
| 8,705,887 B2 | 4/2014 | Ma et al. |
| 8,778,305 B2 | 7/2014 | Pomper et al. |
| 8,855,387 B2 | 10/2014 | Hamadeh et al. |
| 8,962,799 B2 | 2/2015 | Babich et al. |
| 8,995,736 B2 | 3/2015 | Kaufman et al. |
| 9,002,081 B2 | 4/2015 | Brown |
| 9,028,800 B2 | 5/2015 | D'Souza et al. |
| 9,466,133 B2 | 10/2016 | Sowards-Emmerd et al. |
| 9,710,915 B2 | 7/2017 | Firouzian et al. |
| 9,721,340 B2 | 8/2017 | Gillies et al. |
| 10,058,393 B2 | 8/2018 | Bonutti et al. |
| 10,112,974 B2 | 10/2018 | Neumaier et al. |
| 10,140,544 B1 | 11/2018 | Zhao et al. |
| 10,223,610 B1 | 3/2019 | Akselrod-Ballin et al. |
| 10,311,971 B2 | 6/2019 | Opfer et al. |
| 10,330,763 B2 | 6/2019 | James et al. |
| 10,339,653 B2 | 7/2019 | Gillies et al. |
| 10,340,044 B2 | 7/2019 | Yao et al. |
| 10,340,046 B2 | 7/2019 | Baker |
| RE47,609 E | 9/2019 | Hamadeh et al. |
| 10,492,723 B2 | 12/2019 | Madabhushi et al. |
| 10,600,184 B2 | 3/2020 | Golden et al. |
| 10,665,346 B2 | 5/2020 | Baker |
| 10,748,652 B2 | 8/2020 | Yao et al. |
| 10,762,993 B2 | 9/2020 | Baker |
| 10,815,200 B2 | 10/2020 | Cardinale et al. |
| 10,818,386 B2 | 10/2020 | Yao et al. |
| 10,943,681 B2 | 3/2021 | Yao et al. |
| 10,973,486 B2 | 4/2021 | Sjöstrand et al. |
| 11,011,257 B2 | 5/2021 | Lints et al. |
| 11,094,066 B2 | 8/2021 | Nie et al. |
| 11,321,844 B2 | 5/2022 | Johnsson et al. |
| 11,386,988 B2 | 7/2022 | Johnsson et al. |
| 11,424,035 B2 | 8/2022 | Baker |
| 11,508,059 B2 | 11/2022 | Wang et al. |
| 11,534,125 B2 | 12/2022 | Sjöstrand et al. |
| 11,564,621 B2 * | 1/2023 | Anand ............... G06T 7/0012 |
| 11,657,508 B2 | 5/2023 | Richter et al. |
| 11,721,428 B2 | 8/2023 | Brynolfsson et al. |
| 11,894,141 B2 | 2/2024 | Baker |
| 11,900,597 B2 * | 2/2024 | Anand ............... G06N 3/09 |
| 11,937,962 B2 | 3/2024 | Sjöstrand et al. |
| 11,941,817 B2 | 3/2024 | Richter et al. |
| 12,224,067 B1 | 2/2025 | Baker |
| 12,243,236 B1 | 3/2025 | Richter et al. |
| 12,243,637 B2 | 3/2025 | Brynolfsson et al. |
| 2003/0215120 A1 | 11/2003 | Uppaluri et al. |
| 2005/0065421 A1 | 3/2005 | Burckhardt |
| 2005/0281381 A1 | 12/2005 | Guendel |
| 2006/0062425 A1 | 3/2006 | Shen et al. |
| 2006/0064396 A1 | 3/2006 | Wei et al. |
| 2006/0078183 A1 | 4/2006 | deCharms |
| 2007/0081712 A1 | 4/2007 | Huang et al. |
| 2007/0081713 A1 | 4/2007 | Jerebko |
| 2007/0100225 A1 | 5/2007 | Maschke |
| 2007/0115204 A1 | 5/2007 | Budz et al. |
| 2008/0027315 A1 | 1/2008 | McGinnis |
| 2009/0309874 A1 | 12/2009 | Salganicoff et al. |
| 2009/0311182 A1 | 12/2009 | Wang et al. |
| 2010/0032575 A1 | 2/2010 | Lagaru et al. |
| 2010/0080434 A1 | 4/2010 | Seifert et al. |
| 2010/0215581 A1 | 8/2010 | Hoffmann |
| 2010/0266170 A1 | 10/2010 | Khamene et al. |
| 2010/0322488 A1 | 12/2010 | Virtue et al. |
| 2011/0007954 A1 | 1/2011 | Suehling et al. |
| 2011/0063288 A1 | 3/2011 | Valadez |
| 2011/0255763 A1 | 10/2011 | Bogoni et al. |
| 2012/0123253 A1 | 5/2012 | Renisch et al. |
| 2013/0038707 A1 | 2/2013 | Cunningham et al. |
| 2013/0094704 A1 | 4/2013 | Hamadeh et al. |
| 2013/0129168 A1 | 5/2013 | Ross |
| 2013/0211231 A1 | 8/2013 | Sundarapandian et al. |
| 2013/0281841 A1 | 10/2013 | Everett et al. |
| 2014/0105471 A1 | 4/2014 | Brown |
| 2014/0193336 A1 | 7/2014 | Rousso et al. |
| 2015/0003703 A1 | 1/2015 | Franz et al. |
| 2015/0063667 A1 | 3/2015 | Sprencz et al. |
| 2015/0110716 A1 | 4/2015 | Armor |
| 2015/0119704 A1 | 4/2015 | Roth et al. |
| 2015/0287188 A1 | 10/2015 | Gazit et al. |
| 2015/0331995 A1 | 11/2015 | Zhao et al. |
| 2015/0356730 A1 | 12/2015 | Grove et al. |
| 2016/0180042 A1 | 6/2016 | Menon et al. |
| 2016/0203263 A1 | 7/2016 | Maier et al. |
| 2016/0275674 A1 | 9/2016 | Rivet-Sabourin et al. |
| 2016/0335395 A1 | 11/2016 | Wu et al. |
| 2017/0083682 A1 | 3/2017 | McNutt et al. |
| 2017/0112577 A1 | 4/2017 | Bonutti et al. |
| 2018/0140260 A1 | 5/2018 | Taguchi et al. |
| 2018/0144828 A1 | 5/2018 | Baker |
| 2018/0259608 A1 | 9/2018 | Golden et al. |
| 2018/0360402 A1 | 12/2018 | Carmi |
| 2019/0038239 A1 | 2/2019 | Flohr et al. |
| 2019/0105009 A1 | 4/2019 | Siemionow et al. |
| 2019/0105200 A1 | 4/2019 | Hipsley |
| 2019/0209116 A1 | 7/2019 | Sjostrand et al. |
| 2019/0388049 A1 | 12/2019 | Gupta et al. |
| 2020/0027559 A1 | 1/2020 | Baker |
| 2020/0051238 A1 | 2/2020 | El Harouni et al. |
| 2020/0074634 A1 | 3/2020 | Kecskemethy et al. |
| 2020/0085382 A1 | 3/2020 | Taerum et al. |
| 2020/0090328 A1 | 3/2020 | Takei et al. |
| 2020/0097701 A1 | 3/2020 | Chukka et al. |
| 2020/0126666 A1 | 4/2020 | Baker |
| 2020/0170604 A1 | 6/2020 | Yildirim et al. |
| 2020/0193594 A1 | 6/2020 | Georgescu et al. |
| 2020/0193603 A1 | 6/2020 | Golden et al. |
| 2020/0245960 A1 | 8/2020 | Richter et al. |
| 2020/0311919 A1 | 10/2020 | Grimmer et al. |

(56) References Cited

U.S. PATENT DOCUMENTS

| | | |
|---|---|---|
| 2020/0315455 A1 | 10/2020 | Lee et al. |
| 2020/0337658 A1 | 10/2020 | Sjostrand et al. |
| 2020/0342600 A1 | 10/2020 | Sjostrand et al. |
| 2020/0352518 A1 | 11/2020 | Lyman et al. |
| 2020/0357117 A1 | 11/2020 | Lyman et al. |
| 2020/0357118 A1 | 11/2020 | Yao et al. |
| 2020/0357521 A1 | 11/2020 | Baker |
| 2020/0410672 A1 | 12/2020 | Katscher et al. |
| 2021/0032206 A1 | 2/2021 | Neumaier et al. |
| 2021/0082547 A1 | 3/2021 | Yao et al. |
| 2021/0093249 A1 | 4/2021 | Anand et al. |
| 2021/0183485 A1 | 6/2021 | Yao et al. |
| 2021/0233633 A1 | 7/2021 | Lints et al. |
| 2021/0334974 A1 | 10/2021 | Johnsson et al. |
| 2021/0335480 A1 | 10/2021 | Johnsson et al. |
| 2022/0005586 A1 | 1/2022 | Brynolfsson et al. |
| 2022/0375612 A1 | 11/2022 | Baker |
| 2022/0398724 A1 | 12/2022 | Anand et al. |
| 2023/0115732 A1 | 4/2023 | Brynolfsson et al. |
| 2023/0148980 A1 | 5/2023 | Sjöstrand et al. |
| 2023/0316530 A1 | 10/2023 | Richter et al. |
| 2023/0351586 A1 | 11/2023 | Brynolfsson et al. |
| 2023/0410985 A1 | 12/2023 | Brynolfsson et al. |
| 2023/0420112 A1 | 12/2023 | Brynolfsson et al. |
| 2024/0029252 A1 | 1/2024 | Ichinose et al. |
| 2024/0169546 A1 | 5/2024 | Richter et al. |
| 2024/0186010 A1 | 6/2024 | Baker |
| 2024/0285246 A1 | 8/2024 | Sjöstrand et al. |
| 2024/0285248 A1 | 8/2024 | Sjöstrand et al. |
| 2024/0354940 A1 | 10/2024 | Sjöstrand et al. |
| 2025/0061580 A1 | 2/2025 | Richter et al. |
| 2025/0062029 A1 | 2/2025 | Baker |
| 2025/0104225 A1 | 3/2025 | Sjöstrand et al. |

FOREIGN PATENT DOCUMENTS

| | | |
|---|---|---|
| CN | 101528267 A | 9/2009 |
| CN | 101639937 A | 2/2010 |
| CN | 102096804 A | 6/2011 |
| CN | 102361594 A | 2/2012 |
| CN | 102438529 A | 5/2012 |
| CN | 102947840 A | 2/2013 |
| CN | 103607954 A | 2/2014 |
| CN | 103930030 A | 7/2014 |
| CN | 104463840 A | 3/2015 |
| CN | 106127819 A | 11/2016 |
| CN | 106558045 A | 4/2017 |
| CN | 107563378 A | 1/2018 |
| CN | 107644421 A | 1/2018 |
| CN | 114219787 A | 3/2022 |
| EP | 1426903 A2 | 6/2004 |
| EP | 1508872 A1 | 2/2005 |
| EP | 2816525 A1 | 12/2014 |
| EP | 3043318 A1 | 7/2016 |
| EP | 3811845 A1 | 4/2021 |
| GB | 2457577 A | 8/2009 |
| JP | 2010-029481 A | 2/2010 |
| JP | 2011-067594 A | 4/2011 |
| JP | 2012-533384 A | 12/2012 |
| JP | 2014-006130 A | 1/2014 |
| JP | 2015-513083 A | 4/2015 |
| JP | 6013042 B2 | 10/2016 |
| JP | 2017-500537 A | 1/2017 |
| JP | 2017-067489 A | 4/2017 |
| JP | 6170284 B2 | 7/2017 |
| JP | 2017-198697 A | 11/2017 |
| JP | 2019-537714 A | 12/2019 |
| SE | 524500 C2 | 8/2004 |
| TW | 201201847 A | 1/2012 |
| TW | 201825049 A | 7/2018 |
| TW | 201941750 A | 11/2019 |
| TW | 202006742 A | 2/2020 |
| WO | WO-99/05503 A2 | 2/1999 |
| WO | WO-2007/062135 A2 | 5/2007 |
| WO | WO-2009/084995 A1 | 7/2009 |
| WO | WO-2010/071999 A1 | 7/2010 |
| WO | WO-2011/010231 A1 | 1/2011 |
| WO | WO-2011/077303 A1 | 6/2011 |
| WO | WO-2011/091378 A1 | 7/2011 |
| WO | WO-2011/095580 A1 | 8/2011 |
| WO | WO-2013/059177 A1 | 4/2013 |
| WO | WO-2013/126147 A2 | 8/2013 |
| WO | WO-2015/058151 A2 | 4/2015 |
| WO | WO-2016/087592 A1 | 6/2016 |
| WO | WO-2018/014475 A1 | 1/2018 |
| WO | WO-2018/015953 A1 | 1/2018 |
| WO | WO-2018/081354 A1 | 5/2018 |
| WO | WO-2019/005722 A1 | 1/2019 |
| WO | WO-2019/103912 A2 | 5/2019 |
| WO | WO-2019/136349 A2 | 7/2019 |
| WO | WO-2020/144134 A1 | 7/2020 |
| WO | WO-2020/146032 A1 | 7/2020 |
| WO | WO-2020/190821 A1 | 9/2020 |
| WO | WO-2020/219619 A1 | 10/2020 |
| WO | WO-2020/219620 A1 | 10/2020 |
| WO | WO-2021/061315 A1 | 4/2021 |
| WO | WO-2022/008374 A1 | 1/2022 |
| WO | WO-2022/215530 A1 | 10/2022 |
| WO | WO-2023/057411 A9 | 7/2023 |
| WO | WO-2023/239829 A2 | 12/2023 |
| WO | WO-2024/173297 A1 | 8/2024 |
| WO | WO-2024/211651 A1 | 10/2024 |
| WO | WO-2025/072177 A1 | 4/2025 |

OTHER PUBLICATIONS

American College of Radiology (ACR) and the Society for Pediatric Radiology (SPR), ACR-SPR Practice Parameter For The Performance Of Skeletal Scintigraphy (Bone Scan), Resolution 28, (2013-Revused2017), available from: <http://www.acr.org>, 9 pages (2017).

Anand, A. et al., A Pre-Analytical Validation Study of Automated Bone Scan Index: Effect on Accuracy and Reproducibility Due to the Procedural Variabilities in Bone Scan Image Acquisition. J Nucl Med. pp. 1865-1871, (2016).

Anand, A. et al., Analytic Validation of the Automated Bone Scan Index as an Imaging Biomarker to Standardize Quantitative Changes in Bone Scans of Patients with Metastatic Prostate Cancer, J. Nucl. Med., 57(1):41-45 (2016).

Anand, A. et al., Automated Bone Scan Index as a quantitative imaging biomarker in metastatic castration-resistant prostate cancer patients being treated with enzalutamide, EJNMMI Research, 6:23, 7 pages (2016).

Anand, A. et al., Translating Prostate Cancer Working Group 2 (PCWG2) Progression Criteria into a Quantitative Response Biomarker in Metastatic Castration Resistant Prostate Cancer (mCRPC), ASCO GU Conference, Poster, 1 page, presented Feb. 16, 2017.

Anand, A. et al., Translating Prostate Cancer Working Group 2 (PCWG2) progression criteria into a quantitative response biomarker in metastatic castration-resistant prostate cancer (mCRPC), Journal of Clinical Oncology, 35(6):170 (2017).

Armstrong, A. et al., Assessment of the bone scan index in a randomized placebo-controlled trial of tasquinimod in men with metastatic castration-resistant prostate cancer (mCRPC), Urologic Oncology: Seminars and Original Investigations, 32:1308-1316 (2014).

Armstrong, A. et al., Development and validation of a prognostic model for overall survival in chemotherapy-naive men with metastatic castration-resistant prostate cancer (mCRPC) from the phase 3 prevail clinical trial, Journal of Clinical Oncology, 35(Suppl. 6):Abstract 138, 5 pages, (2017).

Armstrong, A. J. et al., Phase 3 Assessment of the Automated Bone Scan Index as a Prognostic Imaging Biomarker of Overall Survival in Men with Metastatic Castration-Resistant Prostate Cancer: A Secondary Analysis of a Randomized Clinical Trial. JAMA Oncology 4:944-951, (2018).

Armstrong, A. J. et al., Phase 3 prognostic analysis of the automated bone scan index (aBSI) in men with bone-metastatic castration-resistant prostate cancer (CRPC), Meeting Library ASC University, 11 pages (2017).

(56) References Cited

OTHER PUBLICATIONS

Bai, P. et. al., Body region localization in whole-body low-dose CT images of PET/CT scans using virtual landmarks, Medical Physics Wiley USA, 46(3): 1286-1299 (2019).

Belal, S. et al., Association of PET Index quantifying skeletal uptake in NaF PET/CT images with overall survival in prostate cancer patients, ASCO GU 2017, Poster 178, 1 page, presented Feb. 16, 2017.

Belal, S. et al., PET Index quantifying skeletal uptake in NaF PET/CT images with overall survival in prostate cancer patients, ASCO GU 2017, Abstract, 1 page, (Feb. 13, 2017).

Belal, S. L. et al, 3D skeletal uptake of 18F sodium fluoride in PET/CT images is associate with overall survival in patients with prostate cancer, EJNMMI Research, 7(15):1-8 (2017).

Belal, S.L. et al., Automated evaluation of normal uptake in different skeletal parts in 18F-sodium fluoride (NaF) PET/CT using a new convolutional neural network method, EJNMMI, EANM '17, 44(Suppl 2):S119-S956, Abstract EP-0116 (2017).

Blue Earth Diagnostics, Posluma Highlights of Prescribing Information, 12 pages, (2023).

Bombardieri, E. et al., Bone scintigraphy: procedure guidelines for tumour imaging, Eur J. Nucl. Med. Mol. Imaging, 30:BP99-BP106, (2003).

Brynolfsson, J., et. al., Deep Learning based urinary bladder segmentation using 18FDCFPyL (PyL-PSMA) PET/CT images, EPS-145, European Association of Nuclear Medicine, (2020), <http://link.springer.com/article/10.1007/s00259-020-04988-4>. pp. S1 and S403-404, Retrieved Sep. 18, 2020.

Brynolfsson, J., et. al., Deep Learning-Enabled comprehensive detection and quantification of 18FDCFPyL (PyL-PSMA) PET/CT, OP-548, European Association of Nuclear Medicine, (2020), <http://link.springer.com/article/10.1007/s00259-020-04988-4>. pp. S1 and S273, Retrieved Sep. 18, 2020.

Bushberg, J. T. et al., Essential Physics of Medical Imaging, Essential Physics of Medical Imaging, 19.3: p. 581 (table 15-3), p. 713 paragraph 6, section 19.3 and p. 720, (2011).

Capobianco, N. et. al., Whole-body uptake classification and prostate cancer staging in $^{68}$Ga-PSMA-11 PET/CT using dual-tracer learning, European Journal of Nuclear Medicine and Molecular Imaging, (2021), <https://doi.org/10.1007/s00259-021-05473-2> 10 pages. Retrieved on Apr. 18, 2021.

Ceci, F. et al., E-PSMA: the EANM standardized reporting guidelines v1.0 for PSMA-PET, European Journal of Nuclear Medicine and Molecular Imaging, 48:1626-1638, (2021).

Cha, K. H., et al. Urinary bladder segmentation in CT urography using deep-learning convolutional neural network and level sets, Medical physics, 43(4):1882-1896, (2016).

Chen, X. et al., TensorMask: A Foundation for Dense Object Segmentation, arXiv, 12 pages, (2019).

Chen, X. et al., TensorMask: A Foundation for Dense Object Segmentation, Proceedings of the IEEE/CVF International Conference on Computer Vision (ICCV), 10 pages, (2019).

Christ, P.F. et al., Automatic Liver and Tumor Segmentation of CT and MRI Volumes Using Cascaded Fully Convolutional Neural Networks, Arxiv.org, Cornell University Library, 20 pages, (2017).

Ciernik, I. F., et al. 3D-segmentation of the 18F-choline PET signal for target volume definition in radiation therapy of the prostate, Technology in cancer research & treatment 6(1): 23-30, (2007).

De Brabandere, B. et al., Semantic Instance Segmentation with a Discriminative Loss Function, arXiv preprint, 10 pages, (2017).

Dennis, E. et al., Bone Scan Index: A Quantitative Treatment Response Biomarker for Castration-Resistant Metastatic Prostate Cancer, Journal of Clinical Oncology, 30(5):519-524 (2012).

Dertat, A., Applied Deep Learning—Part 4: Convolutional Neural Networks, Towards Data Science,<http://towardsdatascience.com/applied-deep-learning-part-4-convolutional-neural-networks-584bc134c1e2> 26 pages, (2017).

Eiber, M. et al., Prostate Cancer Molecular Imaging Standardized Evaluation (PROMISE): Proposed miTNM Classification for the Interpretation of PSMA-Ligand PET/CT, The Journal of Nuclear Medicine, 59(3):469-478, (2018).

Emmett, L. et al., The Primary Score: Using Intraprostatic 68Ga-PSMA PET/CT Patterns to Optimize Prostate Cancer Diagnosis, J. Nucl. Med., 63(11):1644-1650 (2022).

Fendler, W.P. et. al., $^{68}$Ga-PSMA PET/CT: Joint EANM and SNMMI procedure guideline for prostate cancer imaging: version 1.0, Eur J Nucl Med Mol Imaging, DOI 10.1007/s00259-017-3670-z, 11 pages, (2017).

Gafita, A. et al., Novel Framework for Treatment Response Evaluation Using PSMA PET/CT in Patients with Metastatic Castration-Resistant Prostate Cancer (RECIP 1.0): An International Multicenter Study, J. Nucl. Med., 63(11):1651-1658 (2022).

GE Healthcare, SPECT/CT Cameras, 2 pages, retrieved Oct. 25, 2017: <http://www3.gehealthcare.com.sg/en-gb/products/categories/nuclear_medicine/spect-ct_cameras>.

Ghosh, P. and Mitchell, M., Prostate segmentation on pelvic CT images using a genetic algorithm, Proceedings of SPIE, vol. 6914, Medical Imaging 2008: Image Processing, 8 pages, (2008).

Giesel, F. L. et al., F-18 labelled PSMA-1007: biodistribution, radiation dosimetry and histopathological validation of tumor lesions in prostate cancer patients, Eur. J. Nucl. Med. Mol. Imaging, 44:678-688 (2017).

Gjertsson, K., et. al., A Novel Automated Deep Learning Algorithm for Segmentation of the Skeleton in Low-Dose CT for [(18)F] DCFPyL PET/CT Hybrid Imaging in Patients with Metastatic Prostate Cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0823, p. S765.

Gjertsson, K., Segmentation in Skeletal Scintigraphy Images using Convolutional Neural Networks, Master's Theses in Mathematical Sciences, pp. 39-58, (2017), <https://lup.lub.lu.se/student-papers/search/publication/8916406>.

Goffin, K. E. et al., Phase 2 study of $^{99m}$Tc-trofolastat SPECT/CT to identify and localize prostate cancer in intermediate- and high-risk patients undergoing radical prostatectomy and extended pelvic lymph node dissection, J. Nucl. Med., 27 pages (2017).

Gorthi, S. et al., Segmentation of Head and Neck Lymph Node Regions for Radiotherapy Planning Using Active Contour-Based Atlas Registration, IEEE Journal of Selected Topics in Signal Processing, 3(1):135-147 (2009).

Grahovac, M. et al., Machine learning predictive performance evaluation of conventional and fuzzy radiomics in clinical cancer imaging cohorts, Eur. J. Med. Mol. Imaging, 50(6):1607-1620 (2023).

Guan, H. et al., Automatic Hot Spot Detection and Segmentation in Whole Body FDG-PET Images, IEEE International Conference on Image Processing, 4 pages, (2006).

Guimond, A. et al., Average Brain Models: A Convergence Study, Computer Vision and Image Understanding, 77:192-210 (2000).

Hajnal, J. et al., 4.4 Intensity, Size, and Skew Correction; 7.1 Introduction; 7.2 Methods; 7.3 Image Interpretation—General, In: Medical Image Registration, CRC Press LLC, 80-81:144-148 (2001).

Hatamizadeh, A. et al., UNETR: Transformers for 3D Medical Image Segmentation, Proceedings of the IEEE/CVF Winter Conference on Applications of Computer Vision (WACV), 11 pages, (2022).

He, K. et al., Pelvic Organ Segmentation Using Distinctive Curve Guided Fully Convolutional Networks, IEEE Trans. Med. Imaging, 38(2):585-595 (2019).

Hiller, S. M. et al., 99mTc-Labeled Small-Molecule Inhibitors of Prostate-Specific Membrane Antigen for Molecular Imaging of Prostate Cancer, Journal of Nuclear Medicine, 54(8):1369-1376 (2013) retrieved Oct. 25, 2017: <http://jnm.snmjournals.org/content/54/8/1369.full>.

Horikoshi, H. et al., Computer-aided diagnosis system for bone scintigrams from Japanese patients: importance of training database, Annals of Nuclear Medicine, 26(8):622-626 (2012).

Huang, J.-H. et al., A Set of Image Processing Algorithms for Computer-Aided Diagnosis in Nuclear Medicine Whole Body Bone Scan Images, IEEE Transactions on Nuclear Science, 54(3):514-522 (2007).

(56) References Cited

OTHER PUBLICATIONS

Iandola, F.N. et al., SqueezeNet: AlexNet-level accuracy with 50x fewer parameters and <0.5MB model size, arXiv, 13 pages, (2016).
Im, HJ, et. al., et. al., Current Methods to Define Metabolic Tumor Volume in Positron Emission Tomography: Which One is Better?, Nucl. Med. Mol. Imaging, 52(1):5-15, (2018).
Inoue, T., What cancers can be understood and not known by "PET"?—Effects of PET scanning by site, Medical Note Interview, 4 pages, (2015), retrieved from the internet at: https://medicalnote.jp/contents/150715-000003-CYJIZE.
International Search Report for PCT/US2020/047500, filed Aug. 21, 2020, 3 pages, mailed (Mar. 15, 2021).
Invitation to Pay Additional Fees for PCT/EP2022/077505, filed Oct. 4, 2022, 15 pages, (mailed Feb. 2, 2023).
Johnsson, K. et al., Analytical performance of aPROMISE: automated anatomic contextualization, detection, and quantification of [18F]DCFPyL (PSMA) imaging for standardized reporting, European Journal of Nuclear Medicin and Molecular Imaging, 11 pages, Aug. 31, 2021, doi: 10.1007/s00259-021-05497-8. Epub ahead of print. PMID: 34463809.
Johnsson, K., et. al., miPSMA Index: Comprehensive and Automated Quantification of 18F-DCFPyL (PyL-PSMA) PET/CT for Prostate Cancer Staging, J Nucl Med., 61: (Supplement 1): 1435, 5 pages, (2020).
Kaboteh R. et al., Progression of bone metastases in patients with prostate cancer—automated detection of new lesions and calculation of bone scan index, EJNMMI Research, 3:64, 6 pages, (2013).
Kaboteh, R. et al., Convolutional neural network based quantification of choline uptake in PET/CT studies is associated with overall survival in patents with prostate cancer, EJNMMI, EANM '17, 44(Suppl 2):S119-S956, Abstract EP-0642 (2017).
Kawakami, K. et al., Introduction of bone scintigraphy diagnosis support software "Bonenavi" (Topics), Journal of Nuclear Medicine (Japanese), 63:41-51 (2011).
Kawakami, K., Evaluation of bone metastasis by bone scintigraphy diagnostic support software Bonenavi, Communication of the Imaging Group of the JSRT, 36(1):74-77 (2013).
Kertesz, H. et al., Implementation of a Spatially-Variant and Tissue-Dependent Positron Range Correction for PET/CT Imaging, Front. Physiol., 13:818463 (2022).
Kertesz, H. et al., Positron range in combination with point-spread-function correction: an evaluation of different implementations for [124I]-PET imaging, ENJMMI Phys., 9(1):56 (2022).
Khurshid, Z. et al., Role of textural heterogeneity parameters in patient selection for 177Lu-PSMA therapy via response prediction, Oncotarget., 9(70):33312-33321 (2018).
Kiess, et al., Prostate-specific membrane antigen and a target for cancer imaging and therapy, The Quarterly Journal of Nuclear Medicine and Molecular Imaging, 59(3):241-268 (2015).
Kikuchi, A. et al., Automated segmentation of the skeleton in whole-body bone scans: influence of difference in atlas, Nuclear Medicine Communications, 33(9):947-953 (2012).
Kinahan, P.E. et al., PET/CT Standardized Update Values (SUVs) in Clinical Practice and Assessing Response to Therapy, Semin Ultrasound CT MR 31(6):496-505 (2010) retrieved Oct. 25, 2017: <https://www.ncbi.nlm.nih.gov/pmc/articles/PMC3026294/>.
Knutsson, H., and Andersson, M., Morphons: Segmentation using Elastic Canvas and Paint on Priors, IEEE International Conference on Image Processing (ICIP 2005), Genova, Italy, 4 pages (2005).
Kopka, K. et al., Glu-Ureido-Based Inhibitors of Prostate-Specific Membrane Antigen: Lessons Learned During the Development of a Novel Class of Low-Molecular-Weight Theranostic Radiotracers, The Journal of Nuclear Medicine, 58(9)(Suppl. 2):17S-26S, (2017).
Krajnc, D. et al., Automated data preparation for in vivo tumor characterization with machine learning, Front. Oncol., 12:1017911 (2022).
Lin, T.Y. et. al., Feature Pyramid Networks for object detection, FAIR, 10 pages, (2016), <https://arxiv.org/abs/1612.03144v1>.
Litjens, G. et al., A survey on deep learning in medical image analysis, Medical Image Analysis, 42:60-88, (2017).

Liu, L. et al., Computer-Aided Detection of Prostate Cancer with MRI: Technology and Applications, Acad Radiol. Author manuscript, 50 pages 2016.
Ma, L. et al., Automatic segmentation of the prostate on CT images using deep learning and multi-atlas fusion, Proc. of SPIE vol. 10133:101332O-1-101332O-9 (2017).
Ma, L. et al., Combining Population and Patient-Specific Characteristics for Prostate Segmentation on 3D CT Images, Proc of SPIE 9784:978427-1-8 (2016).
Ma, L. et al., Random Walk Based Segmentation for the Prostate on 3D Transrectal Ultrasound Images, Proc SPIE Int Soc Opt Eng. Author manuscript, 13 pages (2016).
Matsubara, N. et al., A Phase II, Randomized, Open-Label, Multi-arm Study of TAS-115 for Castration-Resistant Prostate Cancer Patients With Bone Metastases, Clinical Genitourinary Cancer, 000(xxx):1-10, (2021).
Mayo Clinic Staff, Choline C-11 PET scan, Overview, Mayo Clinic, 4 pages (2017), retrieved Oct. 25, 2017: <https://www.mayoclinic.org/tests-procedures/choline-c-11-pet-scan/home/ovc-20156994>.
Meyer, A., et. al., Deep learning algorithm improves identification of men with low-risk prostate cancer using PSMA targeted 99mTc-MIP-1404 SPECT/CT, Journal of Clinical Oncology, 37:(15), (2019).
Milletari, F. et al., V-Net: Fully Convolutional Neural Networks for Volumetric Medical Image Segmentation, 2016 Fourth International Conference on 3D Vision (3DV), 11 pages, (2016).
Nakajima, K. et al., Enhanced diagnostic accuracy for quantitative bone scan using an artificial neural network system: a Japanese multi-center database project, EJNMMI Research, 3:83, 9 pages, (2013).
National Cancer Institute, NCI Drug Dictionary: gallium Ga 68-labeled PSMA-11, 1 page, retrieved Oct. 25, 2017: <https://www.cancer.gov/publications/dictionaries/cancer-drug?cdrid=766400>.
National Cancer Institute, NCI Drug Dictionary: technetium Tc 99m methylene diphosphonate, 1 page, retrieved Oct. 25, 2017: <https://www.cancer.gov/publications/dictionaries/cancer-drug?cdrid=537722>.
Nickols, N. et al., aPROMISE: A Novel Automated-PROMISE platform to Standardize Evaluation of Tumor Burden in 18F-DCFPyL (PSMA) images of Veterans with Prostate Cancer, Journal of Nuclear Medicine, 26 pages, May 28, 2021, doi: 10.2967/jnumed.120.261863.
Nickols, N.G., et. al., A deep learning algorithm to predict coexisting metastatic disease using intraprostatic [F18]DCFPYL PSMA image alone in veterans with prostate cancer, Journal of Clinical Oncology 38, (Supplement 6), 2020.
Nogi, S. et al., Metastatic bone tumor quantified by computer-assisted diagnosis system of bone scintigraphy, Nuclear Medicine in Clinic, 45(3):35-37 (2012).
Ohlsson, M., et. al., Automated decision support for bone scintigraphy, Computer-based medical systems, pp. 1-6, (2009).
Papp, L. et al., Glioma Survival Prediction with Combined Analysis of In Vivo 11C-MET PET Features, Ex Vivo Features, and Patient Features by Supervised Machine Learning, J. Nucl. Med., 59(6):892-899 (2018).
Papp, L. et al., Optimized Feature Extraction for Radiomics Analysis of 18F-FDG PET Imaging, J. Nucl. Med., 60(6):864-872 (2019).
Papp, L. et al., Supervised machine learning enables non-invasive lesion characterization in primary prostate cancer with [68Ga]Ga-PSMA-11 PET/MRI, Eur. J. Nucl. Mol. Imaging, 48(6):1795-1805 (2021).
Partin, A.W. et al., Combination of prostate-specific antigen, clinical stage, and Gleason score to predict pathological stage of localized prostate cancer. A multi-institutional update, JAMA, 277(18):1445-1451 (1997).
Partin, A.W. et al., The use of prostate specific antigen, clinical stage and Gleason score to predict pathological stage in men with localized prostate cancer, J. Urol., 150(1):110-114 (1993).
Paschalis, A. et al., Prostate-specific Membrane Antigen Heterogeneity and DNA Repair Defects in Prostate Cancer, European Urology, 76(4):469-478, (2019).
Perera, M. et al., Sensitivity, Specificity, and Predictors of Positive 68Ga-Prostate-specific Membrane Antigen Positron Emission Tomog-

(56) References Cited

OTHER PUBLICATIONS raphy in Advanced Prostate Cancer: A Systematic Review and Meta-analysis, European Urology, 70(6):926-937 (2016).
Polymeri, E. et al., Analytical validation of an automated method for segmentation of the prostate gland in CT images, EJNMMI, EANM '17, 44(Suppl 2):S119-S956, Abstract EP-0641 (2017).
Polymeri, E., et. al., Deep learning-based quantification of PET/CT prostate gland uptake: association with overall survival, Clinical Physiology Functional Imaging, DOI: 10.1111/cpf.12611, 40(2):106-113, (2019).
Poulakis, V. et al., Preoperative neural network using combined magnetic resonance imaging variables, prostate specific antigen, and Gleason score to predict prostate cancer recurrence after radical prostatectomy, Eur. Urol., 46(5):571-578 (2004).
Pouliot, F., et. al., Prospective evaluation of a Novel Deep Learning Algorithm (PSMA-AI) in the assessment of 99mTc-MIP-1404 SPECT/CT in patients with low or intermediate risk prostate cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0804, p. S765.
radiologyinfo.org for Patients, Computed Tomography (CT), 2 pages, retrieved Oct. 25, 2017: <https://www.radiologyinfo.org/en/submenu.cfm?pg=ctscan>.
Ren, S., et. al., Faster R-CNN: Towards Real-Time Object Detection with Region Proposal Networks, 14 pages, (2015), <http://image-net.org/challenges/LSVRC/2015/results>.
Ronneberger, O., et. al., U-Net: Convolutional Networks for Biomedical Image Segmentation, Springer International Publishing, pp. 234-241, (2015), <http://lmb.informatik.uni-freiburg.de/>. Published online on Nov. 18, 2015.
Rowe, S. P. et al., PET Imaging of prostate-specific membrane antigen in prostate cancer: current state of the art and future challenges, Prostate Cancer and Prostatic Diseases, pp. 1-8 (2016).
Rowe, S. P. et al., PSMA-Based [$^{18}$F]DCFPyL PET/CT Is Superior to Conventional Imaging for Lesion Detection in Patients with Metastatic Prostate Cancer, Mol Imaging Biol, 18:411-419, (2016).
Sabbatini, P. et al., Prognostic Significance of Extent of Disease in Bone in Patients With Androgen-Independent Prostate Cancer, Journal of Clinical Oncology, 17(3):948-957 (1999).
Sadik, M. et al., 3D prostate gland uptake of 18F-choline— association with overall survival in patients with hormone-naïve prostate cancer, The Journal of Nuclear Medicine, 58(Suppl. 1):Abstract 544, 2 pages, (2017).
Sadik, M. et al., A new computer-based decision-support system for the interpretation of bone scans, Nuclear Medicine Communications, 27(5):417-423 (2006).
Sadik, M. et al., Automated 3D segmentation of the prostate gland in CT images—a first step towards objective measurements of prostate uptake in PET and SPECT images, Journal of Nuclear Medicine, 58(1):1074, (2017).
Sadik, M. et al., Automated quantification of reference levels in liver and mediastinum (blood pool) for the Deauville therapy response classification using FDG-PET/CT in lymphoma patients, EJNMMI, EANM '17, 44(Suppl 2):S119-S956, Abstract EP-0770 (2017).
Sadik, M. et al., Computer-assisted interpretation of planar whole-body bone scans, Journal Nuclear Medicine, 49(12):1958-65, 2008.
Sadik, M. et al., Convolutional neural networks for segmentation of 49 selected bones in CT images show high reproducibility, EJNMMI, EANM '17, 44(Suppl 2):S119-S956, Abstract OP-657 (2017).
Sadik, M. et al., Improved classifications of planar whole-body bone scans using a computer-assisted diagnosis system: a multicenter, multiple-reader, multiple-case study, Journal of Nuclear Medicine, 50(3): 368-75, 2009.
Sadik, M. et al., Variability in reference levels for Deauville classifications applied to lymphoma patients examined with 18F-FDG-PET/CT, EJNMMI, EANM '17, 44(Suppl 2):S119-S956, Abstract EP-0771 (2017).
Sajn, L. et al., Computerized segmentation of whole-body bone scintigrams and its use in automated diagnostics, Computer Methods and Programs in Biomedicine, 80:47-55 (2005).

Salerno, J. et al., Multiparametric magnetic resonance imaging for pre-treatment local staging of prostate cancer: A Cancer Care Ontario clinical practice guideline, Canadian Urological Association Journal, 10(9-10):332-339 (2016).
Santos-Cuevas, C. et al. 99mTc-labeled PSMA inhibitor: Biokinetics and radiation dosimetry in healthy subjects and imaging of prostate cancer tumors in patients, Nuclear Medicine and Biology 52:1-6, (2017).
Seifert, R. et al., Second Version of the Prostate Cancer Molecular Imaging Standardized Evaluation Framework Including Response Evaluation for Clinical Trials (PROMISE V2), Eur. Urol., 83(5):405-412 (2023).
Shi, F. et al., Deep learning empowered volume delineation of whole-body organs-at-risk for accelerated radiotherapy, Nat. Commun., 13(1):6566 (2022).
Sjöstrand K. et al., Statistical regularization of deformation fields for atlas-based segmentation of bone scintigraphy images, MICCAI 5761:664-671 (2009).
Sjöstrand, K., et. al., Automated detection and quantification of Prostatic PSMA uptake in SPECT/CT using a Deep Learning Algorithm for Segmentation of Pelvic Anatomy, The Journal of Nuclear Medicine, 59(1):p. 30, (2018).
Sjostrand, K., et al., Automated Assessment of Prostatic PSMA Expression in SPECT/CT using Deep Convolutional Neural Networks—A Prospectively Planned Retrospective Analysis of Phase 3 Study MIP-1404-3301, The Journal of Nuclear Medicine, 60 (Supplement 1): Abstract 401, 1 page, (2019).
Sluimer, I. et al., Toward Automated Segmentation of the Pathological Lung in CT, IEEE Transactions on Medical Imaging, 24(8):1025-1038 (2005).
Teng, C. et al., Head and neck lymph node region delineation using a hybrid image registration method, 3rd IEEE International Symposium on Biomedical Imaging: Nano to Macro, 4 pages, (2006).
Tian, Z. et al., A fully automatic multi-atlas based segmentation method for prostate MR images, Proc SPIE Int Soc Opt Eng. Author manuscript, 12 pages (2015).
Tian, Z. et al., A supervoxel-based segmentation method for prostate MR images, Med. Phys., 44(2):558-569 (2017).
Tian, Z. et al., Deep convolutional neural network for prostate MR segmentation, Proc. of SPIE 10135:101351L-1-101351L-6 12 pages, (2017).
Tian, Z., et al., Superpixel-based Segmentation for 3D Prostate MR Images, IEEE Trans Med Imaging, Author manuscript, pp. 558-569, (2016).
Trägårdh, E., et. al., RECOMIA—a cloud-based platform for artificial intelligence research in nuclear medicine and radiology, EJNMMI Physics, <https://doi.org/10.1186/s40658-020-00316-9>, 7:51, 12 pages, (2020).
Ulmert, D. et al., A Novel Automated Platform for Quantifying the Extent of Skeletal Tumour Involvement in Prostate Cancer Patients Using the Bone Scan Index, European Urology, 62(1):78-84 (2012).
US Food and Drug Administration, Clinical Trial Endpoints for the Approval of Cancer Drugs and Biologics, 21 pages, (2018).
Valladares, A. et al., A multi-modality physical phantom for mimicking tumor heterogeneity patterns in PET/CT and PET/MRI, Med. Phys., 49(9):5819-5829 (2022).
Wallis, J.W. et. al., Three-dimensional display in nuclear medicine, IEEE Trans Med Imaging, 8(4):297-303, (1989).
Washino, H., Injectable for bone scintigraphy: Technetium hydroxymethylenediphosphonate (99mTc) injection solution (Revised Edition), 9 pages, (2007), retrieved from the internet at:https://rada.or.jp/database/home4/normal/ht-docs/member/synopsis/030292.html#:%7E:text=%E6%A6%82%E8%A6%81).
Wrangsjo, A. et al., Non-rigid Registration Using Morphons, Proceedings of the 14th Scandinavian Conference on Image Analysis (SCIA '05), pp. 501-510 (2005).
Written Opinion for PCT/US2020/047500, filed Aug. 21, 2020, 6 pages, mailed (Mar. 15, 2021).
Yin, T.-K., and Chiu, N.T., A Computer-Aided Diagnosis for Locating Abnormalities in Bone Scintigraphy by a Fuzzy System With a Three-Step Minimization Approach, IEEE Transactions on Medical Imaging, 23(5):639-654 (2004).

(56) References Cited

OTHER PUBLICATIONS

Benitez, C.M. et al., Treatment Response Assessment According to Updated PROMISE Criteria in Patients with Metastatic Prostate Cancer Using an Automated Imaging Platform for Identification, Measurement, and Temporal Tracking of Disease, European Urology Oncology, 9 pages, (2024).

Pizzuto, D.A. et al., The central zone has increased 68Ga-PSMA-11 uptake: "Mickey Mouse ears" can be hot on 68Ga-PSMA-11 PET, Eur. J. Nucl. Med. Mol. Imaging, 45(8):1335-1343 (2018).

Wan, H., Automated Contouring Using Neural Networks, Contour Protege AI White Paper, 3 pages, (2020), <https://go.mimsoftware.com/contour-protegeai-plus/white-paper>.

Afshar-Oromieh, A. et al., Radiation dosimetry of (68)Ga-PSMA-11 (HBED-CC) and preliminary evaluation of optimal imaging timing, Eur. J. Nucl. Med. Mol. Imaging, 43(9):1611-1620 (2016).

Gandaglia, G. et al., Distribution of metastatic sites in patients with prostate cancer: A population-based analysis, Prostate, 74(2):210-216 (2014).

Giesel, F.L. et al., (18)F-Labelled PSMA-1007 shows similarity in structure, biodistribution and tumour uptake to the theragnostic compound PSMA-617, Eur. J. Nucl. Med. Mol. Imaging, 43(10):1929-1930 (2016).

Greenspan, H. et al., Deep Learning in Medical Imaging: Overview and Future Promise of an Exciting New Technique, IEEE Transactions on Medical Imaging, 35(5):1153-1159 (2016).

Guntur, A.R. and Rosen, C.J., Bone as an endocrine organ, Endocr. Pract., 18(5):758-762 (2012).

Kaur, D. and Kaur, Y., Various Image Segmentation Techniques: A Review, International Journal of Computer Science and Mobile Computing, 3(5):809-814 (2014).

Nitta, S. et al., Assisted Diagnosis System by Automatic Extraction of Tumor Candidate Areas from PET/CT Images, Medical Imaging Technology, 24(3):181-190 (2006). English translation included.

Seifert, S. et al., Hierarchical parsing and semantic navigation of full body CT data, Medical Imaging 2009: Image Processing, Proceedings of SPIE vol. 7259, 8 pages, (2009).

Sharma, N. and Aggarwal, L.M., Automated medical image segmentation techniques, J. Med. Phys., 35(1):3-14 (2010).

Shen, D. et al., Deep Learning in Medical Image Analysis, Annu. Rev. Biomed. Eng., 19:221-248 (2017).

Weineisen, M. et al., 68Ga- and 177Lu-Labeled Psma I&T: Optimization of a PSMA—Targeted Theranostic Concept and First Proof-of-Concept Human Studies, J. Nucl. Med., 56(8):1169-1176 (2015).

\* cited by examiner

SYSTEMS AND METHODS FOR ARTIFICIAL INTELLIGENCE-BASED IMAGE ANALYSIS FOR CANCER ASSESSMENT

CROSS REFERENCE TO RELATED APPLICATIONS

This application is a continuation of U.S. patent application Ser. No. 17/762,796, filed on Mar. 23, 2022, now U.S. Pat. No. 11,900,597, which is a U.S. National Stage of PCT Application No. PCT/US2020/047500, filed on Aug. 21, 2020, which claims priority to and benefit of U.S. Non-Provisional application Ser. No. 16/734,609, filed Jan. 6, 2020, and U.S. Provisional Application No. 62/907,180, filed Sep. 27, 2019, the content of each of which is hereby incorporated by reference in its entirety.

FIELD OF THE INVENTION

This invention relates generally to methods and systems, for analysis and/or presentation of medical image data. More particularly, in certain embodiments, the invention relates to methods and systems for determining predicted disease status (e.g., prostate cancer status) and/or a value corresponding to predicted risk of the disease status based on automated analysis of medical image data.

BACKGROUND OF THE INVENTION

Targeted image analysis involves the use of radiolabeled small molecules that bind to specific receptors, enzymes and proteins in the body that are altered during the evolution of disease. After administration to a patient, these molecules circulate in the blood until they find their intended target. The bound radiopharmaceutical remains at the site of disease, while the rest of the agent clears from the body. The radioactive portion of the molecule serves as a beacon so that an image may be obtained depicting the disease location and concentration using commonly available nuclear medicine cameras, known as single-photon emission computerized tomography (SPECT) or positron emission tomography (PET) cameras, found in most hospitals throughout the world. Physicians can then use this information to determine the presence and the extent of disease in a patient. The physician can use this information to provide a recommended course of treatment to the patient and to track the progression of disease.

There are a variety of software-based analytical techniques available for analysis and enhancement of PET and SPECT images that can be used by a radiologist or physician. There are also a number of radiopharmaceuticals available for imaging particular kinds of cancer. Imaging agents used in the art include, among others include, without limitation $^{18}$F—NaF, $^{11}$C-Choline, 2-deoxy-2 [18F] fluoro-d-glucose (FDG), and the like. For example, the small molecule diagnostic 1404 targets the extracellular domain of prostate specific membrane antigen (PSMA), a protein amplified on the surface of >95% of prostate cancer cells and a validated target for the detection of primary and metastatic prostate cancer. 1404 is labeled with technetium-99m, a gamma-emitter isotope that is widely available, relatively inexpensive, facilitates efficient preparation, and has spectrum characteristics attractive for nuclear medicine imaging applications.

Another example radiopharmaceutical is PyL™ (also known as [$^{18}$F]DCFPyL, and 18F-PyL), which is a clinical-stage, fluorinated PSMA-targeted PET imaging agent for prostate cancer. A proof-of-concept study published in the April 2016 issue of the Journal of Molecular Imaging and Biology demonstrated that PET imaging with PyL™ showed high levels of PyL™ uptake in sites of putative metastatic disease and primary tumors, suggesting the potential for high sensitivity and specificity in detecting prostate cancer.

An oncologist may use images from a targeted PET or SPECT study of a patient as input in her assessment of whether the patient has a particular disease, e.g., prostate cancer, what stage of the disease is evident, what the recommended course of treatment (if any) would be, whether surgical intervention is indicated, and likely prognosis. The oncologist may use a radiologist report in this assessment. A radiologist report is a technical evaluation of the PET or SPECT images prepared by a radiologist for a physician who requested the imaging study and includes, for example, the type of study performed, the clinical history, a comparison between images, the technique used to perform the study, the radiologist's observations and findings, as well as overall impressions and recommendations the radiologist may have based on the imaging study results. A signed radiologist report is sent to the physician ordering the study for the physician's review, followed by a discussion between the physician and patient about the results and recommendations for treatment.

Thus, the process involves having a radiologist perform an imaging study on the patient, analyzing the images obtained, creating a radiologist report, forwarding the report to the requesting physician, having the physician formulate an assessment and treatment recommendation, and having the physician communicate the results, recommendations, and risks to the patient. The process may also involve repeating the imaging study due to inconclusive results, or ordering further tests based on initial results.

If an imaging study shows that the patient has a particular disease or condition (e.g., cancer), the physician discusses various treatment options, including surgery, as well as risks of doing nothing or adopting a watchful waiting or active surveillance approach, rather than having surgery.

There are limitations associated with this process, both from the perspective of the physician and from the perspective of the patient. While the radiologist's report is certainly helpful, the physician must ultimately rely on her experience in formulating an assessment and recommendation for her patient. Furthermore, the patient must place a great deal of trust in his physician. The physician may show the patient his PET/SPECT images and may tell the patient a numerical risk associated with various treatment options or likelihood of a particular prognosis, but the patient may very well struggle to make sense of this information. Moreover, the patient's family will likely have questions, particularly if cancer is diagnosed but the patient opts not to have surgery. The patient and/or his family members may search online for supplemental information and may become misinformed about risks of the diagnosed condition. A difficult ordeal may become more traumatic.

Thus, there remains a need for systems and methods for improved automated analysis of medical imaging studies and communication of those results, diagnoses, prognoses, treatment recommendations, and associated risks to a patient.

SUMMARY OF THE INVENTION

Presented herein are systems and methods that provide for automated analysis of medical images to determine a predicted disease status (e.g., prostate cancer status) and/or a value corresponding to predicted risk of the disease status for a subject. In particular, the approaches described herein leverage artificial intelligence (AI) to analyze intensities of voxels in a functional image, such as a PET image, and determine a risk and/or likelihood that a subject's disease, e.g., cancer, is aggressive. In certain embodiments, the AI-based image analysis tools described herein determine a classification representing a predicted likelihood of whether the subject has and/or will develop metastases. In certain embodiments, a value representing a risk of metastases is determined.

The AI-based image analysis technology described herein utilizes image segmentation to identify, within a functional (e.g., PET) image, a subset of voxels lying within volumes identified as corresponding to a particular tissue regions. Intensities of those voxels are then provided as input to a machine learning model that has been trained to predict a likelihood of metastases based on intensity patterns. Notably, the particular tissue regions used are regions where localized disease is typically found. Accordingly, the approaches described herein generate predictions of whether a subject that presents a localized disease (e.g., localized prostate cancer) has and/or will develop aggressive disease, such as metastatic cancer. These predictions are generated in a fully automated fashion and can be used alone, or in combination with other cancer diagnostic metrics (e.g., to corroborate predictions and assessments or highlight potential errors). As such, they represent a valuable tool in support of improved cancer diagnosis and treatment.

In one aspect, the invention is directed to a method for determining a predicted disease status (e.g., prostate cancer status) and/or a value corresponding to predicted risk of the disease status based on automated analysis of intensities of a three-dimensional (3D) functional image (e.g., a nuclear medicine image), the method comprising: (a) receiving, by a processor of a computing device, a 3D anatomical image of a subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (b) identifying, by the processor, within the 3D anatomical image, a volume of interest (VOI) corresponding to a prostate region of the subject; (c) receiving, by the processor, a 3D functional image of the subject obtained using a functional imaging modality [e.g., single-photon emission computed tomography (SPECT); e.g., positron emission tomography (PET)][e.g., wherein the 3D functional image comprises a plurality of voxels, each representing a particular physical volume within the subject and having an intensity value that represents detected radiation emitted from a the particular physical volume, wherein at least a portion of the plurality of voxels of the 3D functional image represent physical volumes within one or more of the target tissue regions of the subject]; and (d) determining, by the processor, a predicted disease status of the subject and/or a value corresponding to predicted risk of the disease status of the subject [e.g., wherein the disease status is aggressive disease, e.g., metastatic disease, e.g., metastatic prostate cancer, e.g., one or more types of metastases (e.g., N-type metastases, e.g., M-type metastases)] using a machine learning module that receives, as input, intensities of voxels of the 3D functional image identified as corresponding to the target VOI of the anatomical image.

In certain embodiments. the method comprises identifying the voxels of the 3D functional image corresponding to the target VOI of the anatomical image by: identifying, by the processor, within the 3D functional image, a 3D prostate volume corresponding to the target VOI identified within the 3D anatomical image (e.g., by mapping the target VOI identified within the 3D anatomical image to the 3D functional image) and identifying voxels of the 3D functional image lying within the 3D prostate volume as corresponding to the target VOI of the anatomical image.

In certain embodiments, the machine learning module receives, as input, intensities of only the voxels of the 3D functional image identified as corresponding to the target VOI of the anatomical image, and does not receive, as input, intensities of other voxels of the 3D functional image [e.g., from other regions of the 3D functional image (e.g., that correspond to regions of the anatomical image outside the target VOI)].

In certain embodiments, the machine learning module receives, as input, only intensities of the voxels of the 3D functional image identified as corresponding to the target VOI of the anatomical image (e.g., and no other input).

In certain embodiments, the machine learning module further receives, as input, one or more clinical variables. In certain embodiments, the one or more clinical variables comprise one or more members selected from the group consisting of: a race/ethnicity [e.g., a value (e.g., a numeric value) representing a particular race and/or ethnicity]; a prostate specific antigen (PSA) level and/or velocity; a hemoglobin level; a lactate dehydrogenase level; an albumin level; a clinical T stage [e.g., a TNM staging system code (e.g., an alphanumeric code) and/or a numeric value representing a particular TNM code]; a biopsy Gleason score (e.g., a primary Gleason score; e.g., a secondary Gleason score); and a percentage positive core score [e.g., a value representing a proportion of a plurality of samples collected via biopsy that were identified (e.g., by a pathologist) as positive for prostate cancer].

In certain embodiments, the method comprises determining the predicted disease status, wherein the predicted disease status is a classification corresponding to a prediction of aggressive disease status [e.g., aggressive disease or not; (e.g., whether the subject's prostate cancer is or will become aggressive)].

In certain embodiments, the classification comprises one or more of the following classes corresponding to predictions of whether the subject has and/or likely will develop one or more metastases: an overall metastases class, wherein assignment to the overall metastases class corresponds to a prediction that the subject has and/or will likely develop one or more metastases; one or more particular metastases class, each corresponding to a particular type of metastases (e.g., N-type, e.g., M-type) wherein assignment to the particular metastases class corresponds to a prediction that the subject has and/or will likely develop the particular type of metastases; and a no metastases class, wherein assignment to the no metastases class corresponds to a prediction that the subject had not and/or is not likely to develop one or more metastases.

In certain embodiments, the machine learning module generates, as output, one or more likelihood values representing likelihood(s) of overall metastases (e.g., likelihood of metastases of any kind) and/or one or more particular types of metastases, and wherein determining the classification comprises comparing the one or more likelihood values with one or more thresholds.

In certain embodiments, the method comprises determining the value corresponding to predicted risk of the disease status of the subject, and wherein the disease status is an aggressive disease status (e.g., an aggressive prostate cancer status). In certain embodiments, the value (corresponding to predicted risk of the disease status of the subject) represents a likelihood that the subject has and/or will develop one or more metastases (e.g., prostate cancer metastases). In certain embodiments, the value (corresponding to predicted risk of the disease status of the subject) represents a likelihood that the subject has and/or will develop one or more of a particular type of metastases (e.g., N-type metastases, e.g., M-type metastases).

In certain embodiments, the method comprises determining a plurality of values (corresponding to predicted risk of the disease status of the subject), each corresponding to a particular type of metastases and representing a likelihood that the subject has and/or will develop one or more of the particular type of metastases.

In certain embodiments, the disease is prostate cancer.

In certain embodiments, the machine learning module comprises a convolutional neural network (CNN) (e.g., a fully convolutional neural network).

In certain embodiments, the anatomical image is a CT scan. In certain embodiments, the functional image is a PET image obtained following administration of a radiopharmaceutical to the subject. In certain embodiments, the radiopharmaceutical comprises a prostate specific membrane antigen (PSMA) binding agent. In certain embodiments, the PSMA binding agent is [18F]DCFPyL. In certain embodiments, the functional image is a SPECT image.

In another aspect, the invention is directed to a system for determining a predicted disease status (e.g., prostate cancer status) and/or a value corresponding to predicted risk of the disease status based on automated analysis of intensities of a three-dimensional (3D) functional image (e.g., a nuclear medicine image), the system comprising: a processor of a computing device; and a memory having instructions stored thereon, wherein the instructions, when executed by the processor, cause the processor to: (a) receive a 3D anatomical image of a subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (b) identify, within the 3D anatomical image, a volume of interest (VOI) corresponding to a prostate region of the subject; (c) receive a 3D functional image of the subject obtained using a functional imaging modality [e.g., single-photon emission computed tomography (SPECT); e.g., positron emission tomography (PET)][e.g., wherein the 3D functional image comprises a plurality of voxels, each representing a particular physical volume within the subject and having an intensity value that represents detected radiation emitted from a the particular physical volume, wherein at least a portion of the plurality of voxels of the 3D functional image represent physical volumes within one or more of the target tissue regions of the subject]; and (d) determine a predicted disease status of the subject and/or a value corresponding to predicted risk of the disease status of the subject [e.g., wherein the disease status is aggressive disease, e.g., metastatic disease, e.g., metastatic prostate cancer, e.g., one or more types of metastases (e.g., N-type metastases, e.g., M-type metastases)] using a machine learning module that receives, as input, intensities of voxels of the 3D functional identified as corresponding to the target VOI of the anatomical image.

In certain embodiments, the instructions cause the processor to identify the voxels of the 3D functional image corresponding to the target VOI of the anatomical image by: identifying, within the 3D functional image, a 3D prostate volume corresponding to the target VOI identified within the 3D anatomical image (e.g., by mapping the target VOI identified within the 3D anatomical image to the 3D functional image) and identifying voxels of the 3D functional image lying within the 3D prostate volume as corresponding to the target VOI of the anatomical image.

In certain embodiments, the machine learning module receives, as input, intensities of only the voxels of the 3D functional image identified as corresponding to the target VOI of the anatomical image, and does not receive, as input, intensities of other voxels of the 3D functional image [e.g., from other regions of the 3D functional image (e.g., that correspond to regions of the anatomical image outside the target VOI)].

In certain embodiments, the machine learning module receives, as input, only intensities of the voxels of the 3D functional image identified as corresponding to the target VOI of the anatomical image (e.g., and no other input).

In certain embodiments, the machine learning module further receives, as input, one or more clinical variables. In certain embodiments, the one or more clinical variables comprise one or more members selected from the group consisting of: a race/ethnicity [e.g., a value (e.g., a numeric value) representing a particular race and/or ethnicity]; a prostate specific antigen (PSA) level and/or velocity; a hemoglobin level; a lactate dehydrogenase level; an albumin level; a clinical T stage [e.g., a TNM staging system code (e.g., an alphanumeric code) and/or a numeric value representing a particular TNM code]; a biopsy Gleason score (e.g., a primary Gleason score; e.g., a secondary Gleason score); and a percentage positive core score [e.g., a value representing a proportion of a plurality of samples collected via biopsy that were identified (e.g., by a pathologist) as positive for prostate cancer].

In certain embodiments, at step (d), the instructions cause the processor to determine the predicted disease status, wherein the predicted disease status is a classification corresponding to a prediction of aggressive disease status [e.g., aggressive disease or not; (e.g., whether the subject's prostate cancer is or will become aggressive)]. In certain embodiments the classification comprises one or more of the following classes corresponding to predictions of whether the subject has and/or likely will develop one or more metastases: an overall metastases class, wherein assignment to the overall metastases class corresponds to a prediction that the subject has and/or will likely develop one or more metastases; one or more particular metastases class, each corresponding to a particular type of metastases (e.g., N-type, e.g., M-type) wherein assignment to the particular metastases class corresponds to a prediction that the subject has and/or will likely develop the particular type of metastases; and a no metastases class, wherein assignment to the no metastases class corresponds to a prediction that the subject had not and/or is not likely to develop one or more metastases.

In certain embodiments, the machine learning module generates, as output, one or more likelihood values representing likelihood(s) of overall metastases (e.g., likelihood of metastases of any kind) and/or one or more particular types of metastases, and wherein determining the classification comprises comparing the one or more likelihood values with one or more thresholds.

In certain embodiments, at step (d), the instructions cause the processor to determine the value corresponding to predicted risk of the disease status of the subject, and wherein the disease status is an aggressive disease status (e.g., an aggressive prostate cancer status).

In certain embodiments, the value (corresponding to predicted risk of the disease status of the subject) represents a likelihood that the subject has and/or will develop one or more metastases (e.g., prostate cancer metastases).

In certain embodiments, the value (corresponding to predicted risk of the disease status of the subject) represents a likelihood that the subject has and/or will develop one or more of a particular type of metastases (e.g., N-type metastases, e.g., M-type metastases).

In certain embodiments, the instructions cause the processor to determine a plurality of values (corresponding to predicted risk of the disease status of the subject), each corresponding to a particular type of metastases and representing a likelihood that the subject has and/or will develop one or more of the particular type of metastases.

In certain embodiments, the disease is prostate cancer. In certain embodiments, the machine learning module comprises a convolutional neural network (CNN) (e.g., a fully convolutional neural network). In certain embodiments, the anatomical image is a CT scan.

In certain embodiments, the functional image is a PET image obtained following administration of a radiopharmaceutical to the subject. In certain embodiments, the radiopharmaceutical comprises a prostate specific membrane antigen (PSMA) binding agent. In certain embodiments, the PSMA binding agent is [18F]DCFPyL. In certain embodiments, the functional image is a SPECT image.

In another aspect, the invention is directed to a method for determining a predicted disease status of the subject and/or a value corresponding to predicted risk of the disease status of the subject based on automated analysis of intensities of a three-dimensional (3D) functional image (e.g., a nuclear medicine image), the method comprising: (a) receiving, by a processor of a computing device, a 3D anatomical image of a subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (b) identifying, by the processor, within the 3D anatomical image, a first volume corresponding to a target tissue volume of interest (VOI) of the subject (e.g., a prostate region, e.g., a brain region, e.g., a breast region, e.g., a lung region, e.g., a liver region, e.g., a colon region, e.g., a stomach region) (e.g., using a segmentation technique); (c) receiving, by the processor, a 3D functional image of the subject obtained using a functional imaging modality [e.g., single-photon emission computed tomography (SPECT); e.g., positron emission tomography (PET)][e.g., wherein the 3D functional image comprises a plurality of voxels, each representing a particular physical volume within the subject and having an intensity value that represents detected radiation emitted from the particular physical volume, wherein a subset of the plurality of voxels of the 3D functional image corresponds the target tissue VOI of the subject]; and (d) determining, by the processor, a predicted disease status and/or a value corresponding to a predicted risk of the disease status [e.g., wherein the disease status is aggressive disease, e.g., metastatic disease, e.g., metastatic prostate cancer, e.g., one or more types of metastases (e.g., N-type, e.g., M-type)] using a machine learning module that receives, as input, intensities of voxels of the 3D functional image identified as corresponding to the first volume of the 3D anatomical image and one or more clinical variables selected from the group consisting of: a race/ethnicity [e.g., a value (e.g., a numeric value) representing a particular race and/or ethnicity]; a prostate specific antigen (PSA) level and/or velocity; a hemoglobin level; a lactate dehydrogenase level; an albumin level; a clinical T stage [e.g., a TNM staging system code (e.g., an alphanumeric code) and/or a numeric value representing a particular TNM code]; a biopsy Gleason score (e.g., a primary Gleason score; e.g., a secondary Gleason score); and a percentage positive core score [e.g., a value representing a proportion of a plurality of samples collected via biopsy that were identified (e.g., by a pathologist) as positive for prostate cancer].

In certain embodiments, the method comprises identifying the voxels of the 3D functional image corresponding to the first volume of the 3D anatomical image by: automatically identifying, by the processor, within the 3D functional image, a second volume corresponding to the first volume identified within the 3D anatomical image (e.g., by mapping the first volume identified within the 3D anatomical image to the 3D functional image) and identifying voxels of the 3D functional image lying within the second volume as corresponding to the first volume of the anatomical image.

In certain embodiments, the machine learning module receives, as input, intensities of only the voxels of the 3D functional image identified as corresponding to the target VOI of the anatomical image, and does not receive, as input, intensities of other voxels of the 3D functional image [e.g., from other regions of the 3D functional image (e.g., that correspond to regions of the anatomical image outside the target VOI)].

In certain embodiments, the method comprises determining the predicted disease status, wherein the predicted disease status is a classification corresponding to a prediction of aggressive disease status.

In certain embodiments, the classification comprises one or more of the following classes corresponding to predictions of whether the subject has and/or likely will develop one or more metastases: an overall metastases class, wherein assignment to the overall metastases class corresponds to a prediction that the subject has and/or will likely develop one or more metastases; one or more particular metastases class, each corresponding to a particular type of metastases wherein assignment to the particular metastases class corresponds to a prediction that the subject has and/or will likely develop the particular type of metastases; and a no metastases class, wherein assignment to the no metastases class corresponds to a prediction that the subject had not and/or is not likely to develop one or more metastases.

In certain embodiments, the machine learning module generates, as output, one or more likelihood values representing likelihood(s) of overall metastases and/or one or more particular types of metastases, and wherein determining the classification comprises comparing the one or more likelihood values with one or more thresholds.

In certain embodiments, the method comprises determining the value corresponding to predicted risk of the disease status of the subject, and wherein the disease status is an aggressive disease status.

In certain embodiments, the value represents a likelihood that the subject has and/or will develop one or more metastases. In certain embodiments, the value represents a likelihood that the subject has and/or will develop one or more of a particular type of metastases. In certain embodiments, the method comprises determining a plurality of values, each corresponding to a particular type of metastases and representing a likelihood that the subject has and/or will develop one or more of the particular type of metastases.

In certain embodiments, the disease is prostate cancer.

In certain embodiments, the machine learning module comprises a convolutional neural network (CNN). In certain embodiments, the anatomical image is a CT scan. In certain embodiments, the functional image is a PET image obtained following administration of a radiopharmaceutical to the subject. In certain embodiments, the radiopharmaceutical comprises a prostate specific membrane antigen (PSMA) binding agent. In certain embodiments, the PSMA binding agent is [18F]DCFPyL. In certain embodiments, the functional image is a SPECT image.

In another aspect, the invention is directed to a system for determining a predicted disease status of the subject and/or a value corresponding to predicted risk of the disease status of the subject based on automated analysis of intensities of a three-dimensional (3D) functional image (e.g., a nuclear medicine image), the system comprising: a processor of a computing device; and a memory having instructions stored thereon, wherein the instructions, when executed by the processor, cause the processor to: (a) receive a 3D anatomical image of a subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (b) identify, within the 3D anatomical image, a first volume corresponding to a target tissue volume of interest (VOI) of the subject (e.g., a prostate region, e.g., a brain region, e.g., a breast region, e.g., a lung region, e.g., a liver region, e.g., a colon region, e.g., a stomach region)(e.g., using a segmentation technique); (c) receive a 3D functional image of the subject obtained using a functional imaging modality [e.g., single-photon emission computed tomography (SPECT); e.g., positron emission tomography (PET)] [e.g., wherein the 3D functional image comprises a plurality of voxels, each representing a particular physical volume within the subject and having an intensity value that represents detected radiation emitted from the particular physical volume, wherein a subset of the plurality of voxels of the 3D functional image corresponds the target tissue VOI of the subject]; and (d) determine a predicted disease status and/or a value corresponding to a predicted risk of the disease status [e.g., wherein the disease status is aggressive disease, e.g., metastatic disease, e.g., metastatic prostate cancer, e.g., one or more types of metastases (e.g., N-type, e.g., M-type)] using a machine learning module that receives, as input, intensities of voxels of the 3D functional image identified as corresponding to the first volume of the 3D anatomical image and one or more clinical variables selected from the group consisting of: a race/ethnicity [e.g., a value (e.g., a numeric value) representing a particular race and/or ethnicity]; a prostate specific antigen (PSA) level and/or velocity; a hemoglobin level; a lactate dehydrogenase level; an albumin level; a clinical T stage [e.g., a TNM staging system code (e.g., an alphanumeric code) and/or a numeric value representing a particular TNM code]; a biopsy Gleason score (e.g., a primary Gleason score; e.g., a secondary Gleason score); and a percentage positive core score [e.g., a value representing a proportion of a plurality of samples collected via biopsy that were identified (e.g., by a pathologist) as positive for prostate cancer].

In certain embodiments, the instructions cause the processor to identify the voxels of the 3D functional image corresponding to the first volume of the 3D anatomical image by: automatically identifying, within the 3D functional image, a second volume corresponding to the first volume identified within the 3D anatomical image (e.g., by mapping the first volume identified within the 3D anatomical image to the 3D functional image) and identifying voxels of the 3D functional image lying within the second volume as corresponding to the first volume of the anatomical image.

In certain embodiments, the machine learning module receives, as input, intensities of only the voxels of the 3D functional image identified as corresponding to the target VOI of the anatomical image, and does not receive, as input, intensities of other voxels of the 3D functional image [e.g., from other regions of the 3D functional image (e.g., that correspond to regions of the anatomical image outside the target VOI)].

In certain embodiments, at step (d), the instructions cause the processor to determine the predicted disease status, wherein the predicted disease status is a classification corresponding to a prediction of aggressive disease status.

In certain embodiments, the classification comprises one or more of the following classes corresponding to predictions of whether the subject has and/or likely will develop one or more metastases: an overall metastases class, wherein assignment to the overall metastases class corresponds to a prediction that the subject has and/or will likely develop one or more metastases; one or more particular metastases class, each corresponding to a particular type of metastases wherein assignment to the particular metastases class corresponds to a prediction that the subject has and/or will likely develop the particular type of metastases; and a no metastases class, wherein assignment to the no metastases class corresponds to a prediction that the subject had not and/or is not likely to develop one or more metastases.

In certain embodiments, the machine learning module generates, as output, one or more likelihood values representing likelihood(s) of overall metastases and/or one or more particular types of metastases, and wherein determining the classification comprises comparing the one or more likelihood values with one or more thresholds.

In certain embodiments, at step (d), the instructions cause the processor to determine the value corresponding to predicted risk of the disease status of the subject, and wherein the disease status is an aggressive disease status. In certain embodiments, the value represents a likelihood that the subject has and/or will develop one or more metastases. In certain embodiments, the value represents a likelihood that the subject has and/or will develop one or more of a particular type of metastases. In certain embodiments, the instructions cause the processor to determine a plurality of values, each corresponding to a particular type of metastases and representing a likelihood that the subject has and/or will develop one or more of the particular type of metastases.

In certain embodiments, the disease is prostate cancer.

In certain embodiments, the machine learning module comprises a convolutional neural network (CNN). In certain embodiments, the anatomical image is a CT scan. In certain embodiments, the functional image is a PET image obtained following administration of a radiopharmaceutical to the subject. In certain embodiments, the radiopharmaceutical comprises a prostate specific membrane antigen (PSMA) binding agent. In certain embodiments, the PSMA binding agent is [18F]DCFPyL. In certain embodiments, the functional image is a SPECT image Features of embodiments described with respect to one aspect of the invention may be applied with respect to another aspect of the invention.

BRIEF DESCRIPTION OF THE FIGURES

The foregoing and other objects, aspects, features, and advantages of the present disclosure will become more apparent and better understood by referring to the following description taken in conjunction with the accompanying drawings, in which.

Figure 1:
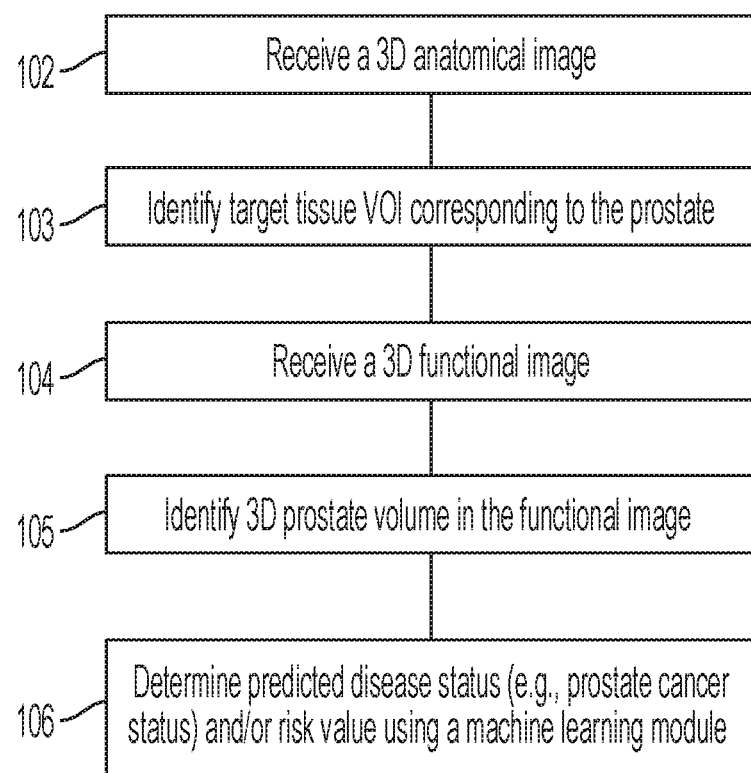
FIG. 1 is a block flow diagram of a process for determining a prostate cancer status of a subject using the AI-based approaches described herein, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

Image: As used herein, the term "image", for example, as in a three-dimensional image of a patient, includes any visual representation, such as a photo, a video frame, streaming video, as well as any electronic, digital, or mathematical analogue of a photo, video frame, or streaming video. Any apparatus described herein, in certain embodiments, includes a display for displaying an image or any other result produced by a processor. Any method described herein, in certain embodiments, includes a step of displaying an image or any other result produced by the method.

3D, three-dimensional: As used herein, "3D" or "three-dimensional" with reference to an "image" means conveying information about three spatial dimensions. A 3D image may be rendered as a dataset in three dimensions and/or may be displayed as a set of two-dimensional representations, or as a three-dimensional representation. In certain embodiments, a 3-D image is represented as voxel (e.g., volumetric pixel) data.

Radionuclide: As used herein, "radionuclide" refers to a moiety comprising a radioactive isotope of at least one element. Exemplary suitable radionuclides include but are not limited to those described herein. In some embodiments, a radionuclide is one used in positron emission tomography (PET). In some embodiments, a radionuclide is one used in single-photon emission computed tomography (SPECT). In some embodiments, a non-limiting list of radionuclides includes $^{99m}$Tc, $^{111}$In, $^{64}$Cu, $^{67}$Ga, $^{68}$Ga, $^{186}$Re, $^{188}$Re, $^{153}$Sm, $^{177}$Lu, $^{67}$Cu, $^{123}$I, $^{124}$I, $^{125}$I, $^{126}$I, $^{131}$I, $^{11}$C, $^{13}$N, $^{15}$O, $^{18}$F, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{105}$Rh, $^{111}$Ag, $^{89}$Zr, $^{225}$Ac, $^{82}$Rb, $^{75}$Br, $^{76}$Br, $^{77}$Br, $^{80}$Br, $^{80}$Br, $^{82}$Br, $^{83}$Br, $^{211}$At and $^{192}$Ir.

Radiopharmaceutical: As used herein, the term "radiopharmaceutical" refers to a compound comprising a radionuclide. In certain embodiments, radiopharmaceuticals are used for diagnostic and/or therapeutic purposes. In certain embodiments, radiopharmaceuticals include small molecules that are labeled with one or more radionuclide(s), antibodies that are labeled with one or more radionuclide(s), and antigen-binding portions of antibodies that are labeled with one or more radionuclide(s).

Subject: As used herein, a "subject" means a human or other mammal (e.g., rodent (mouse, rat, hamster), pig, cat, dog, horse, primate, rabbit, and the like).

Administering: As used herein, "administering" an agent means introducing a substance (e.g., an imaging agent) into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments.

Filter, filtering, filtering function: As used herein, the terms "filter", and "filtering", as in a "filtering function" or a "filter", refer to a function that operates on localized portions of an input array (e.g., a multi-dimensional array) of data (e.g., image data, e.g., values computed by a layer of a CNN), referred to herein as "subpatches", computing, for a given subpatch, a response value. In general, a filter is applied in a sliding window fashion across the array to compute a plurality of response values for the array. In particular, for a given multidimensional array, a subpatch of the array can be a rectangular region of the array having a specific size (e.g., having the same number of dimensions as the array). For example, for a 6×3×3 array, a given 3×3×3 subpatch refers to a given 3×3×3 set of adjacent values (e.g., a neighborhood) of the array, such that there are five distinct 3×3×3 subpatches in the 6×3×3 array (each patch shifted one position over along the first dimension).

For example, a filtering function can compute, for a given subpatch of an array, a response value using the values of the subpatch. A filtering function can be applied in a sliding window fashion across an array, computing, for each of a plurality of subpatches of the array, a response value. The computed response values can be stored in an output array such that the positional correspondence between response values and the subpatches of the input array is maintained.

For example, at a first step, beginning with a subpatch in a corner of an input array, a filter can compute a first response value, and store the first response value in a corresponding corner of an output array. In certain embodiments, at a second step, the filter then computes a second response value for a second subpatch, shifted one position over along a specific dimension of the input array. The second response value can be stored in a corresponding position of the output array—that is, shifted one position over along a same dimension of the output array. The step of shifting position of the subpatch, computing a response value, and storing the response value in a corresponding position of the output array can be repeated for the full input array, along each dimension of the input array. In certain embodiments (e.g., a strided filtering approach), the subpatch for which the filter computes a response value is shifted more than one position at a time along a given dimension, such that response values are not computed for every possible subpatch of the input array.

Convolutional neural network (CNN): As used herein, the term "convolutional neural network (CNN)" refers to a type of artificial neural network where at least one layer performs one or more filtering functions. As used herein, the term "convolution layer" refers to a layer of a CNN that receives as input an input array and computes an output array, wherein values of the output array are computed by applying one or more filters to the input array. In particular, in certain embodiments, a convolution layer receives as input an input array having n+1 dimensions and produces an output array also having n+1 dimensions. The first n dimensions of input and output arrays operated on by filtering layers of a CNN are referred to herein as "spatial dimensions". The $(n+1)^{th}$ dimension of the input is referred to herein as the "input channel" dimension. The size of the input channel dimension is referred to herein as the "number of input channels". The $(n+1)^{th}$ dimension of the output is referred to herein as the "output channel" dimension. The size of the input channel dimension is referred to herein as the "number of output channels".

In certain embodiments, a convolution layer computes response values by applying a filter that operates on subpatches that are smaller than the input array along the spatial dimensions, but extend across the full output channel dimension. For example, an N×M×L×$K_0$ size input array, has three spatial dimensions and $K_0$ output channels. Filters of a convolution layer may operate on subpatches having sizes of $N_f$×$M_f$×$L_f$×$K_0$, where $N_f$≤N, $M_f$≤M and $L_f$≤L. Often, a filter of a convolutional layer operates on subpatches having sizes where $N_f$<N, $M_f$<M and/or $L_f$<L. For example, in certain embodiments, $N_f$<<N, $M_f$<<M and/or $L_f$<<L.

Accordingly, for each of one or more filters applied by a convolution layer, response values computed by a given filter are stored in a corresponding output channel. Accordingly, a convolution layer that receives an input array having n+1 dimensions computes an output array also having n+1 dimensions, wherein the $(n+1)^{th}$ dimension represents the output channels corresponding to the one or more filters applied by the convolution layer. In this manner, an output array computed by a given convolution layer can be received as input by a subsequent convolution layer.

Size (of a filter of a convolution layer): As used herein, the term "size" in reference to a filter of a convolution layer refers to a size along spatial dimensions of subpatches on which the filter operates (e.g., the subpatch size along the output channel dimension is taken as the full number of output channels). As used herein, the term "size", in reference to a convolution layer, as in "size of a convolution layer" refers to a size of filters of the convolution layer (e.g., each filter of the convolution layer having a same size). In certain embodiments, a filter of a convolution layer has a number of variable parameters that are determined via a machine learning training process. In certain embodiments, the number of parameters of a given filter equals the number of values in a subpatch that the given filter operates on. For example, a size $N_f$×$M_f$×$L_f$ filter that operates on an input array with $K_0$ output channels has $N_f$×$M_f$×$L_f$×$K_0$ parameters. In certain embodiments, a filter is implemented as an array, and the response value determined by the filter for a given subpatch is computed as a dot product between the filter and the given subpatch.

Fully convolutional neural network (FCNN): As used herein, the term "fully convolutional neural network (FCNN)" refers to a CNN wherein each layer of the CNN is a convolution layer.

Volume (input or output of a CNN layer): As used herein, the term "volume", as used in reference to an input or output of a layer of a CNN refers to an input array received or an output array computed by a CNN layer.

CNN module: As used herein, the term "CNN module" refers to a computer implemented process that implements a specific CNN in order to determine, for a given input, such as an image (e.g., a 2D image; e.g., a 3D image) one or more output values. For example, a CNN module may receive as input a 3D image of a subject (e.g., a CT image; e.g., an MRI), and for each voxel of the image, determine a value that represents a likelihood that the voxel lies within a region of the 3D image that corresponds to a representation of a particular organ or tissue of the subject. A CNN module may be software and/or hardware. For example, a CNN module may be implemented entirely as software, or certain functions of a CNN module may be carried out via specialized hardware (e.g., via an application specific integrated circuit (ASIC)).

Tissue: As used herein, the term "tissue" refers to bone (osseous tissue) as well as soft-tissue.

Full body, whole body: As used herein, the terms "full body" and "whole body" used (interchangeably) in the context of segmentation refer to approaches that evaluate a majority (e.g., greater than 50%) of a graphical representation of a subject's body in a 3D anatomical image to identify target tissue regions of interest. In certain embodiments, full body and whole body segmentation refers to identification of target tissue regions within at least an entire torso of a subject. In certain embodiments, portions of limbs are also included, along with a head of the subject.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

A. Artificial Intelligence-Based Image Analysis for Prediction of Disease Status and Aggressiveness Described herein are systems and methods that utilize Artificial Intelligence (AI)—namely, machine learning modules that implement machine learning algorithms such as convolutional neural networks (CNNs)—to analyze intensity patterns in functional images in order to determine a predicted disease status of a subject and/or a value corresponding to predicted risk of the disease status. As described herein, the AI-based image analysis tools of the present disclosure can be used to predict cancer aggressiveness based on analysis of images of localized disease. For example, as described in further detail below, intensity patterns within an imaged volume corresponding a prostate region of a subject can be used to determine a prediction of whether the disease has and/or will progress to an aggressive status, e.g., with the subject developing metastases outside the prostate where localized disease is found.

The approaches described herein may be utilized to evaluate other types of cancer, such as brain, breast, lung, liver, colon, and stomach cancer (e.g., by analyzing intensity patters in imaged volumes corresponding to brain, breast, lung, liver, colon, and stomach regions, respectively).

In providing this functionality, the approaches described herein generate predictions of disease status in a fully automated fashion. These predictions can be used alone, or in combination with other cancer diagnostic metrics, to, e.g., corroborate predictions and assessments or highlight potential errors. As such, they represent a valuable tool in support of improved cancer diagnosis and treatment.

A.i Image Segmentation and Extraction of Prostate Intensities

FIG. 1 shows an example process 100 for determining a predicted disease status and/or value corresponding to a risk of predicted disease status via the AI approaches described herein. In a first step 102, a three-dimensional (3D) anatomical image is received. The 3D anatomical image is obtained using an anatomical imaging modality, such as computed tomography (CT) or magnetic resonance (MR) imaging. The detailed anatomical information of the anatomical image allows it to be used for accurate identification of volumes of interest (VOIs) that correspond to specific tissue regions. At step 103, a target tissue VOI corresponding to the prostate of the subject is identified.

A variety of approaches can be used for identification of target tissue VOIs (e.g., for image segmentation). On example approach that is particularly attractive utilizes a deep-learning technique based on neural networks. This approach and its application to identify target VOIs corresponding to the prostate is described in detail in PCT Publication WO 2019/136349, incorporated herein by reference in its entirety. In particular, in certain embodiments, one or more CNNs are used to segment an anatomical image to identify target VOIs. A single CNN may be used or, in certain cases, multiple CNN's may be used to segment multiple target VOIs, and/or partition an initial (e.g., whole body) anatomical image into manageable sub-volumes (initial VOIs) corresponding to general anatomical regions, for example via a coarse segmentation. These manage-able sub-volumes can then be further segmented, finely, at high resolution, to identify specific target VOIs that represent specific tissue regions of interest.

Figure 2A:
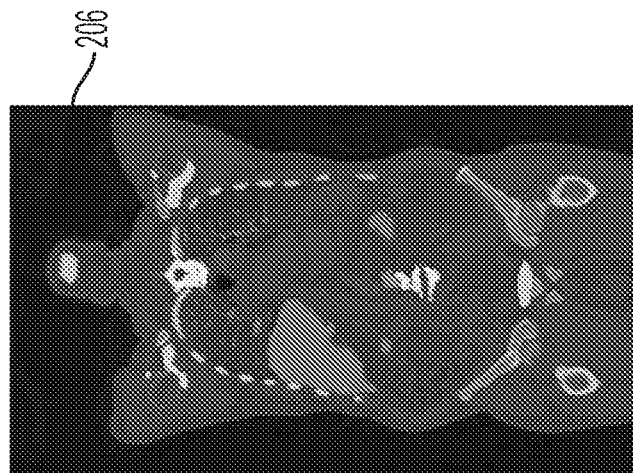
FIG. 2A is a schematic illustrating segmentation of an anatomical (e.g., a CT) image, according to an illustrative embodiment.
Figure 2A:
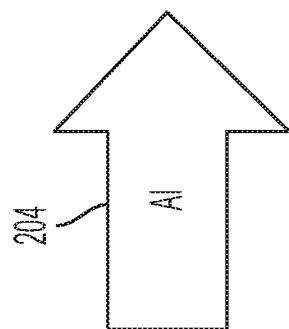
Figure 2A:
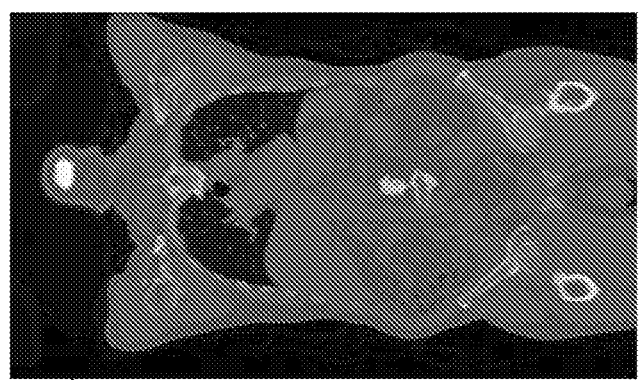

Use of this image segmentation approach is illustrated in further detail in FIG. 2A. As shown in the workflow 200 in the figure, a CT image 202 is input to an image segmentation machine learning module 204, which outputs a segmentation map 206 comprising one or more segmentation masks that identify various tissue VOIs corresponding to different specific physical tissue regions.

Figure 2B:
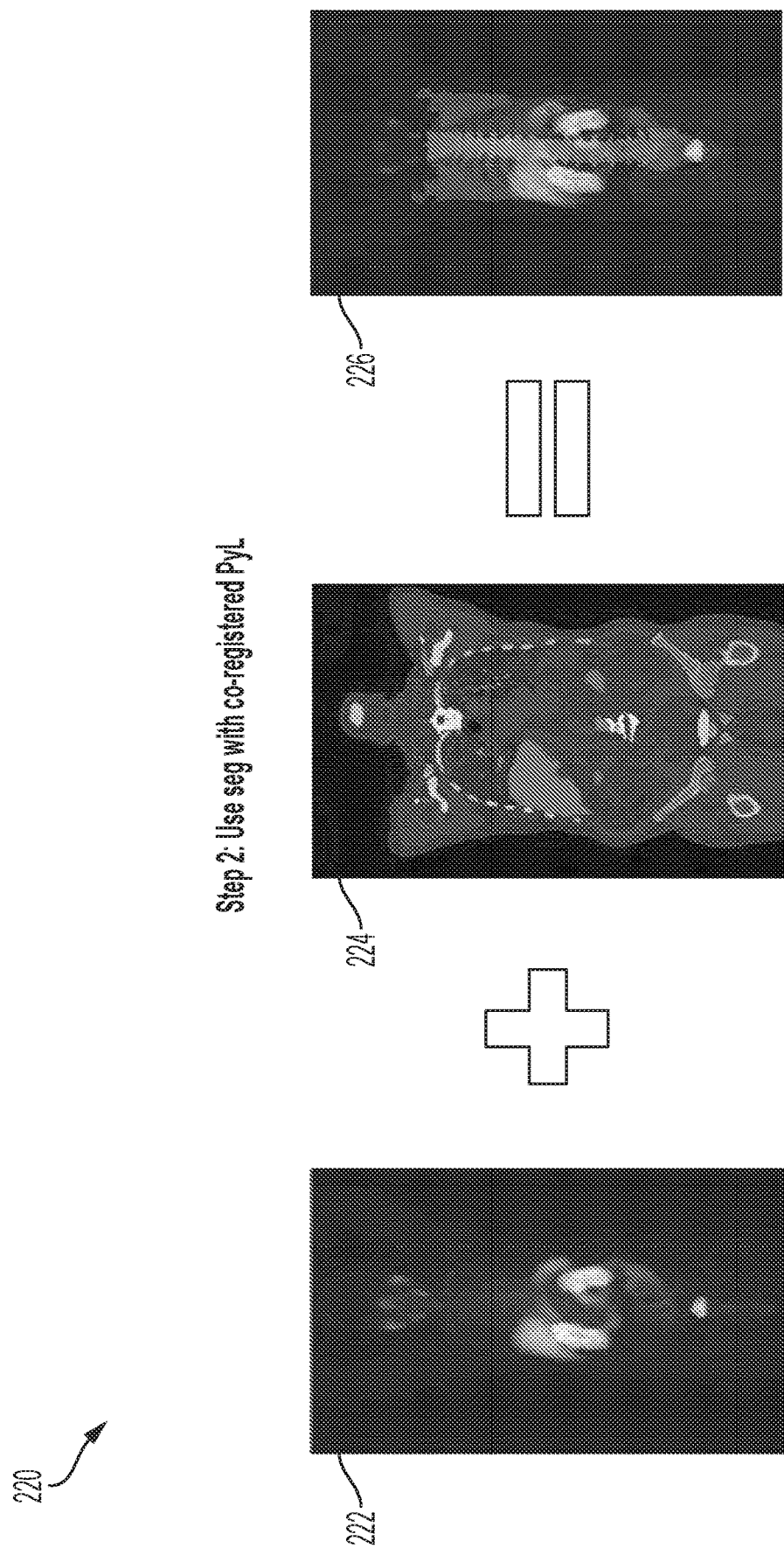
FIG. 2B is a schematic illustrating mapping a target volume of interest (VOI) from an anatomical (e.g., CT) image to a functional (e.g., PET) image, according to an illustrative embodiment.

Once the anatomical image is segmented, the target tissue VOIs identified in the anatomical image are mapped to a 3D functional image to identify corresponding 3D volumes. In particular, in another step, a 3D functional image 222, such as positron emission tomography (PET) image or a single photon emission tomography (SPECT) image is received 104. The identified target tissue VOI from the anatomical is used to identify a corresponding 3D prostate volume in the received functional image 105. FIG. 2B shows an example process 220 in which 3D volumes corresponding to identified target tissue VOIs are identified in a 3D functional image. As shown in FIG. 2B, in certain embodiments, a segmentation mask 224 comprising multiple segmentation masks (e.g., not just one that identifies a prostate region) can be co-registered with a 3D functional image 222 and used to identify the 3D prostate volume, as well as other volumes in the functional image 226.

Figure 2C:
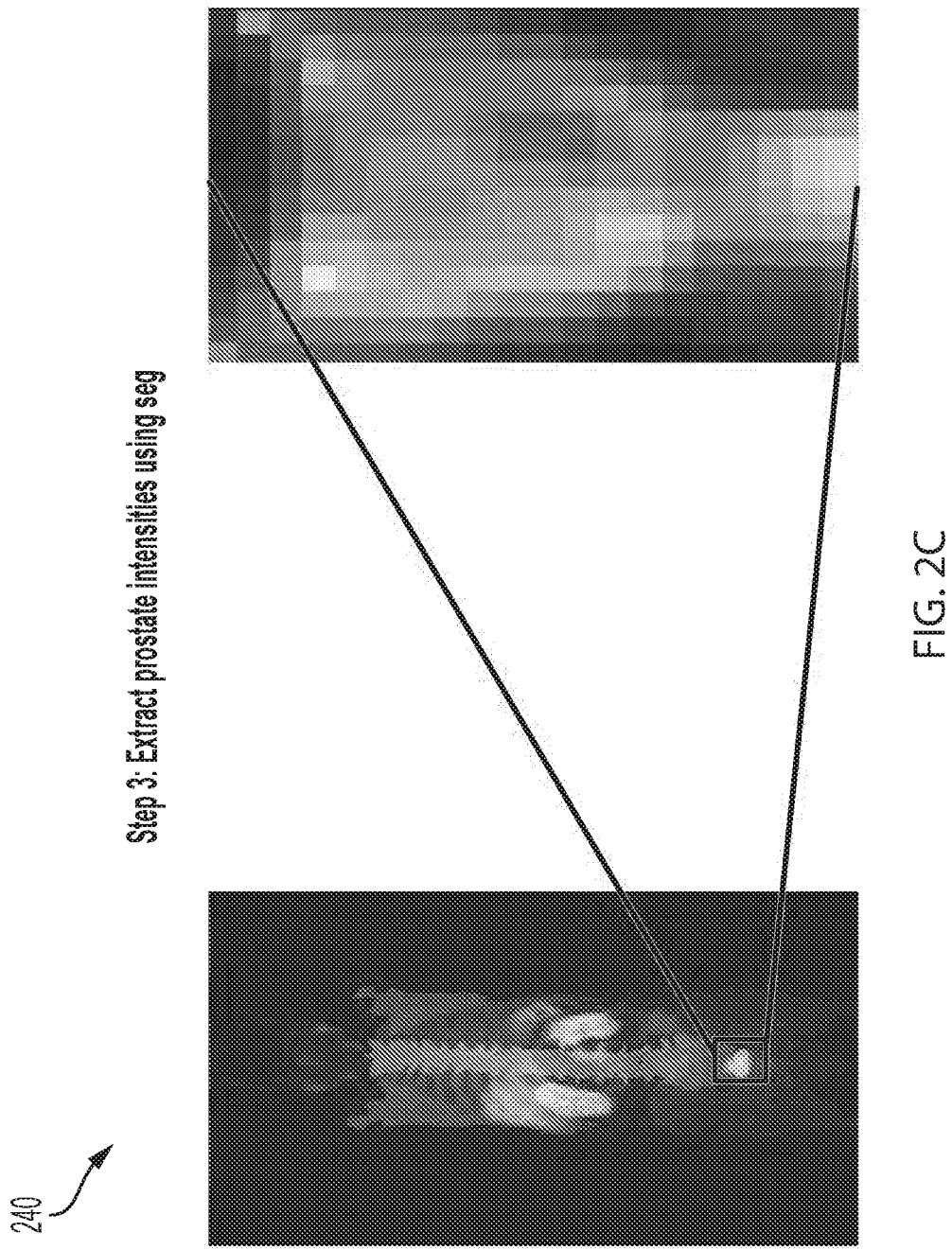
FIG. 2C is a schematic illustrating extracting intensities within a 3D prostate volume of a functional (e.g., PET) image, according to an illustrative embodiment.

In another step 106, intensities of voxels within the 3D prostate volume are used as input to a machine learning module to determine a prostate cancer status for the subject. In certain embodiments, as shown in FIG. 2C, in certain embodiments, these prostate intensities are extracted 240 from the functional image for use as input to the machine learning module.

Figure 2D:
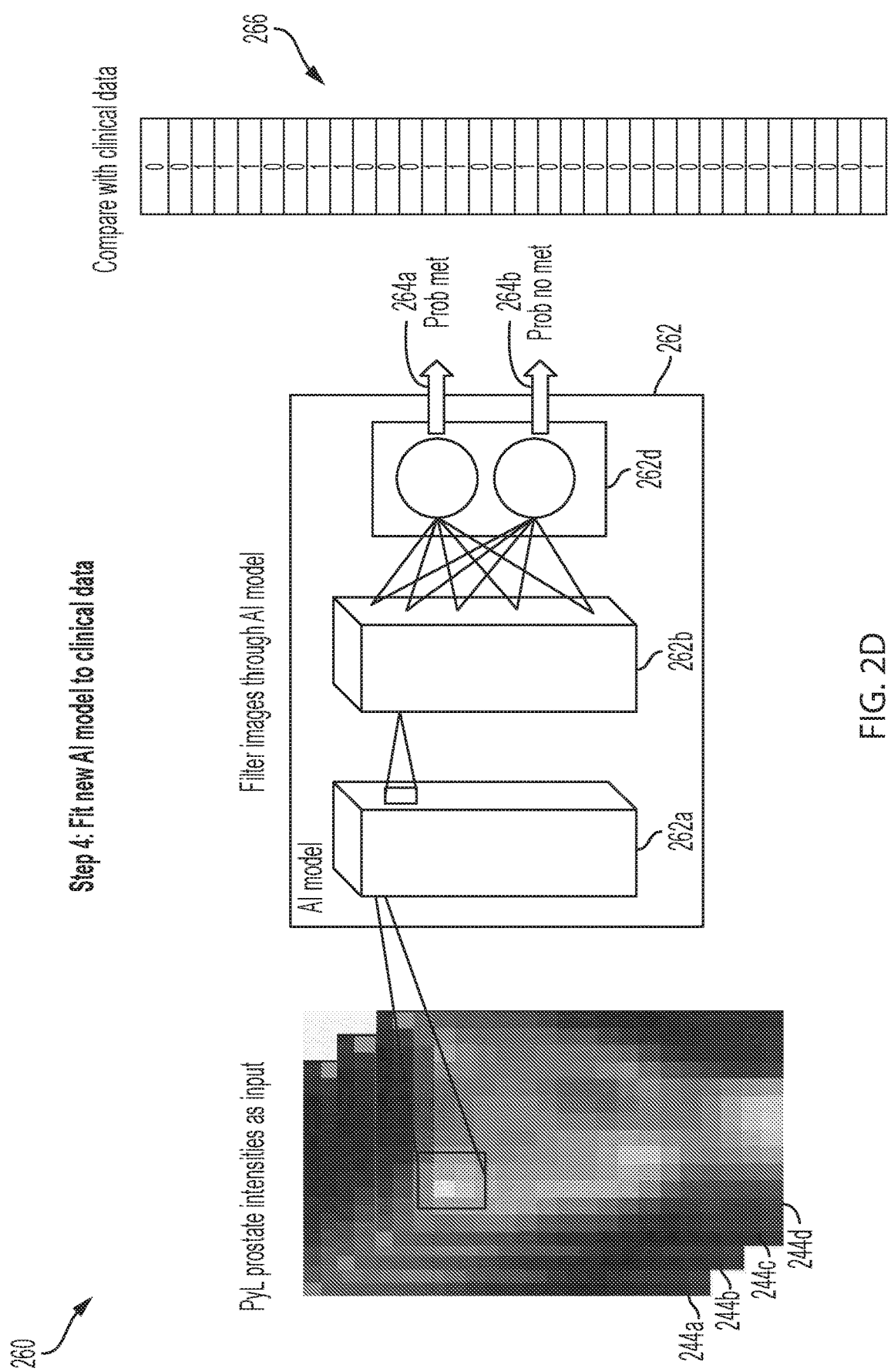
FIG. 2D is a schematic illustrating use of intensities of functional image voxels lying within a 3D prostate volume as inputs into a machine learning network to determine a prostate cancer status for a subject, according to an illustrative embodiment.

FIG. 2D shows a diagram of an example process 260 wherein prostate intensities 244a, 244b, 244c, 244d are used as input to a machine learning module 262 to perform a binary classification that assigns a cancer status of probably metastatic 264a or not 264b. Various layers 262a, 262b, and 262d of the machine learning module 262 are shown schematically. As shown in FIG. 2D, clinical data 266 can be used to train and test a module to perform a desired classification.

Figure 3:
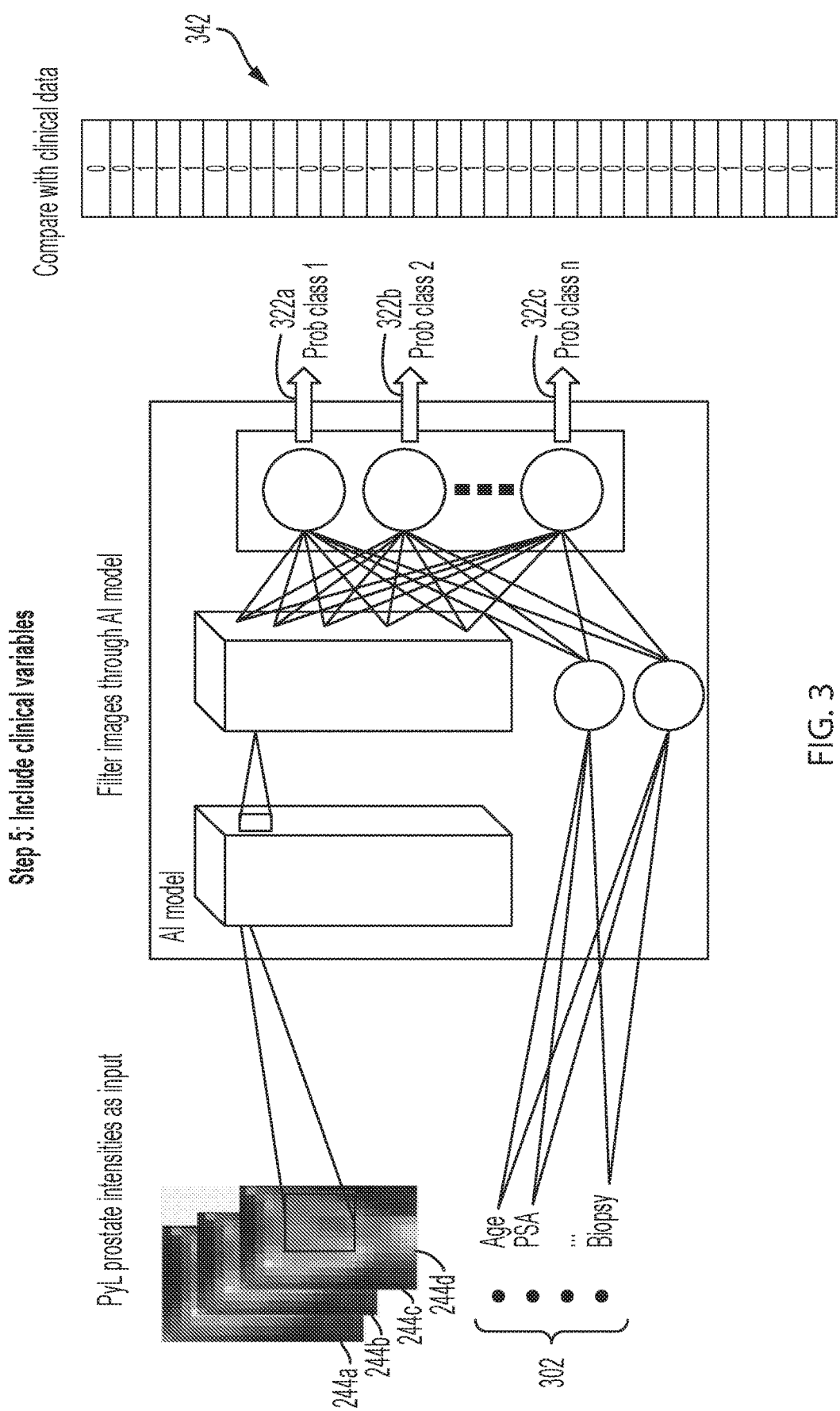
FIG. 3 is a schematic of illustrating additional input and output options for a machine learning module used to determine a prostate cancer status of a subject, according to an illustrative embodiment.

In certain embodiments, in addition to prostate volume intensities, the machine learning module may take other information as input. For example, as shown in FIG. 3, clinical variables 302, such as age, prostate-specific antigen (PSA) level and/or velocity, biopsy score, and others may be used. Measurements of additional biomarkers, such as hemoglobin, lactate dehydrogenase, and albumin may also be used.

In certain embodiments, a machine learning module may perform a non-binary classification, such that the output assigns a subject's prostate cancer to one of several classes, e.g., 322a, 322b, 322c. For example, a more detailed classification of metastases can performed that differentiates between N-stage (indicating metastases to lymph nodes) and M-stage (indicating metastases in regions other than the lymph nodes) metastases. For example, three classes—no metastases, N-stage, and M-stage can be used. As with the approach illustrated in FIG. 2D, clinical data 342 can be used to train and test the machine learning module to perform a desired classification.

A.ii Machine Learning Module Implementation and Training

Figure 4A:
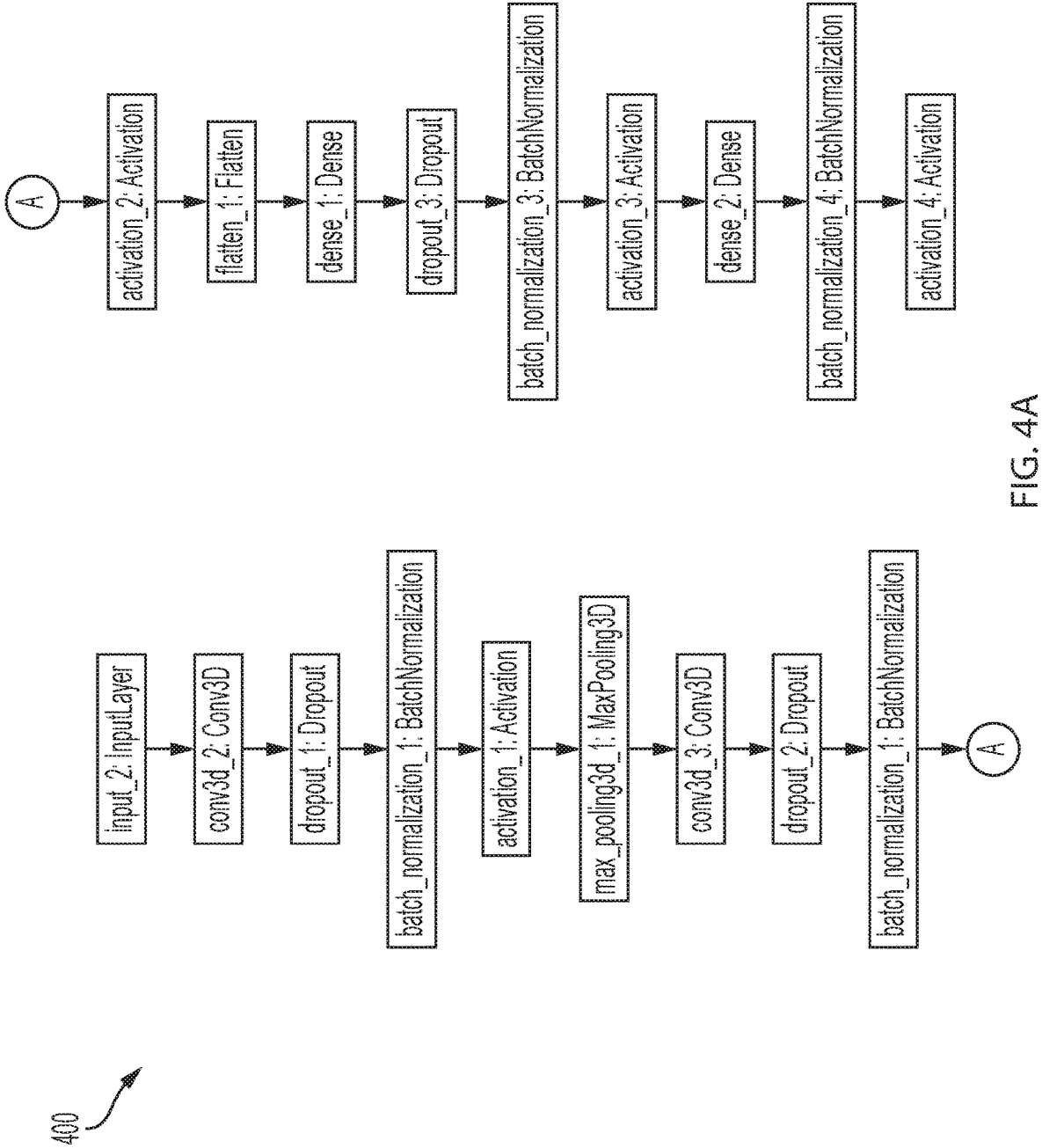
FIG. 4A is a block flow diagram of a Convolutional Neural Network (CNN) implemented via a machine learning module that takes prostate volume intensities as input and performs a binary classification of prostate cancer status, according to an illustrative embodiment.
Figure 4B:
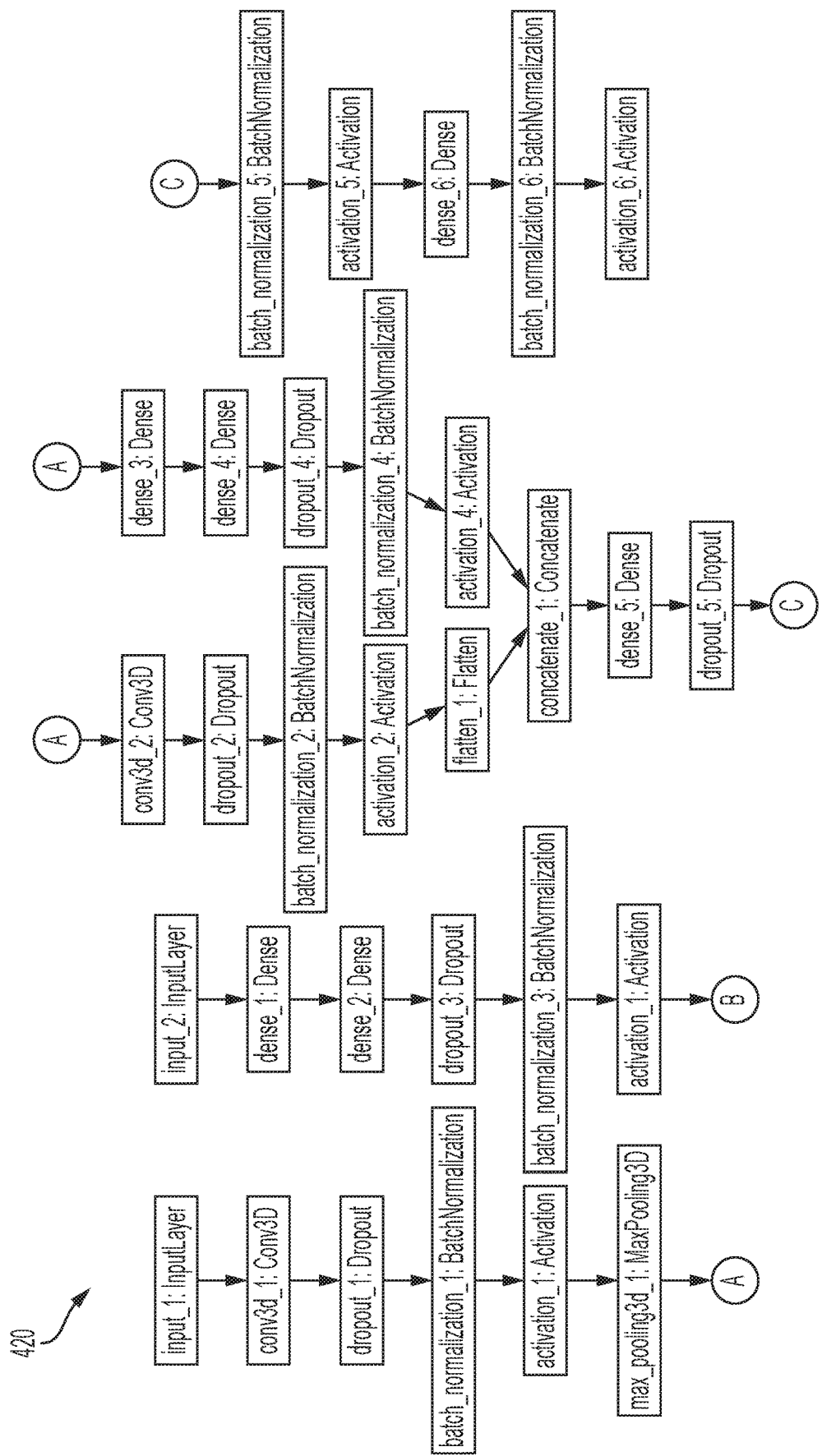
FIG. 4B is a block flow diagram of an Artificial Neural Network (ANN) implemented via a machine learning module that takes (i) prostate volume intensities and (ii) clinical variables as input and performs a binary classification of prostate cancer status, according to an illustrative embodiment.

In an illustrative embodiment, the approaches described herein were used to develop, train, and test machine learning modules to analyze prostate volume intensities in PET images obtained following administration of PyL™ as a radiopharmaceutical. The machine learning modules implemented were used to perform a binary classification of a subject's prostate cancer positive or negative for predicted metastases. Two different prediction modules were implemented and trained. A first prediction module used only intensities of voxels in a prostate volume identified in the PET images, while a second prediction module also utilized prostate volume intensities, but included clinical variables as well. FIG. 4A shows detailed structure of a first convolutional neural network (CNNs) 400 implemented by the first machine learning prediction module. FIG. 4B shows detailed structure of a second CNN 420 implemented by the second machine learning prediction module.

The first CNN included a number of convolutional layers (2 layers), followed by a dense layer with 64 nodes and another dense layer with 2 nodes. The second CNN, which also utilized clinical variables as input, used a similar architecture as the first, but with an additional dense branch for processing the clinical variable values. This clinical variable value branch used 4 dense layers with 128, 64, 128 and 64 nodes, which are later merged with a dense layer of 64 nodes, also used in the first CNN.

Each convolutional layer in the CNNs is followed by a dropout regularization layer (using a dropout factor of 0.5) and a max pooling layer reducing each spatial dimension with a factor 2. Each layer (both dense and convolutional) is followed by a batch normalization layer and the non-linear relu activation function, except for the dense layers in the clinical variable values branch with 128 nodes and the final dense layer with 2 nodes which uses a softmax activation instead of a relu.

In order to extract prostate volume intensities from PET images, an implementation of the approach described in PCT Publication WO 2019/136349, incorporated herein by reference in its entirety was used segment CT images of a PET/CT image pair, map a target VOI corresponding to the prostate to a PET image, and identify, within the PET image, a 3D prostate volume. The segmentation approach also utilizes CNNs to identify the 3D prostate VOI within the CT image. In particular, a localization module implements one CNN to perform a coarse segmentation on the anatomical image to identify an initial VOI corresponding to a pelvic region. A secondary, fine segmentation module implements a CNN that operates on the initial VOI to identify, within the initial VOI, a prostate VOL The prostate VOI identified in the anatomical image is then mapped to the PET image, to identify a corresponding 3D prostate volume in the PET image.

Both prediction modules were trained and tested using images obtained from patients with a known metastatic state—i.e., that were known to not have metastases, or to have metastases, either in lymph nodes (N-type) or other parts of the body (M-type). Training was performed using an Adam optimizer (https://arxiv.org/abs/1412.6980v8) and a binary cross entropy loss function.

Each machine learning prediction module output a value between 0 and 1, where values approaching 1 indicated higher probability/certainty that an imaged and analyzed patient has (i.e., is positive for) metastases. This output value was compared to a discrimination threshold to perform a binary classification of positive or negative for metastases (e.g., if the value was below the discrimination threshold, the patient was classified as negative, and if it was above, the patient was classified as positive for metastases).

Figure 5A:
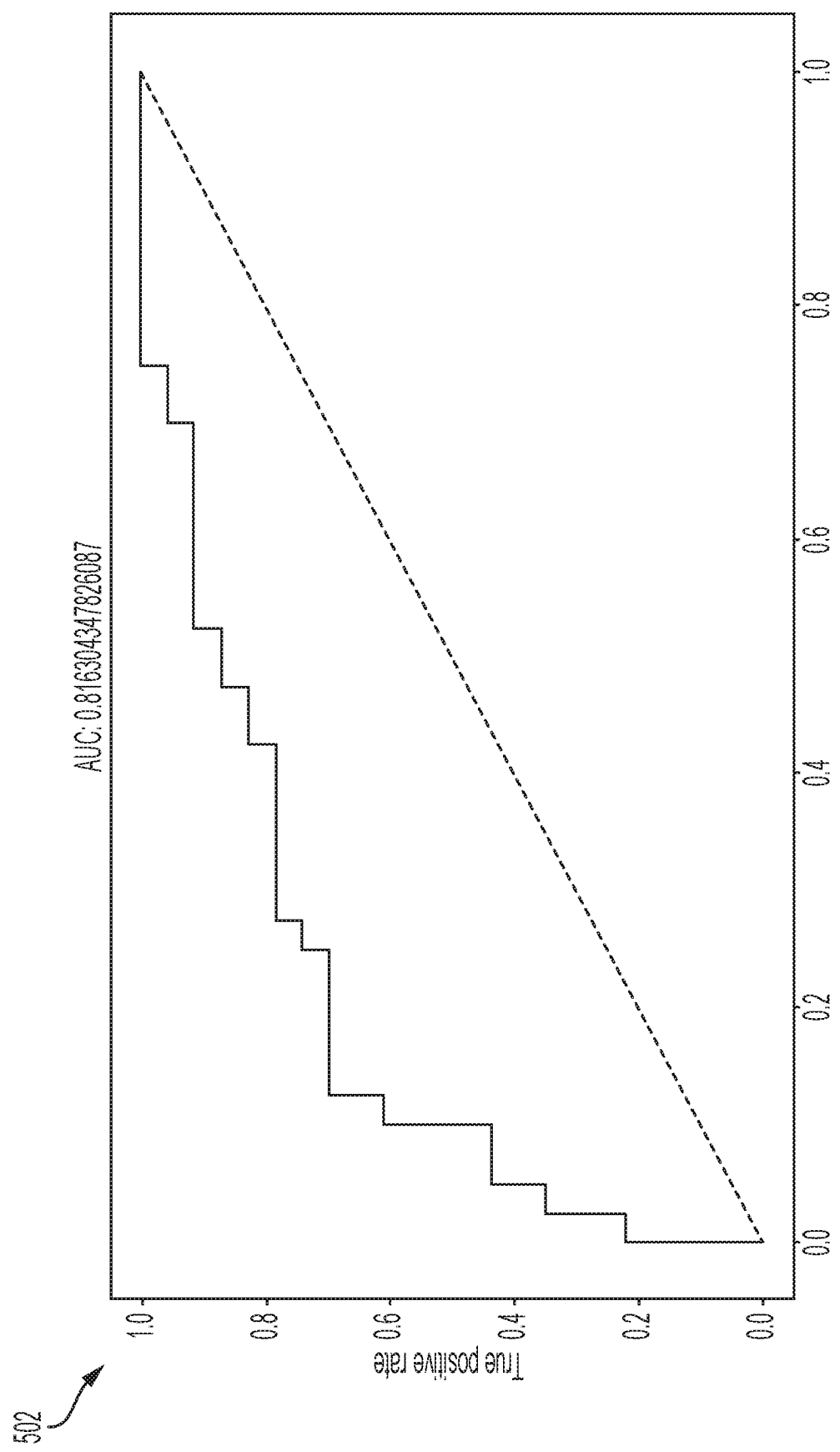
FIG. 5A is a graph of a receiver operating characteristic (ROC) curve for a binary classification of prostate cancer metastases using a machine learning module that takes prostate volume intensities as input.
Figure 5B:
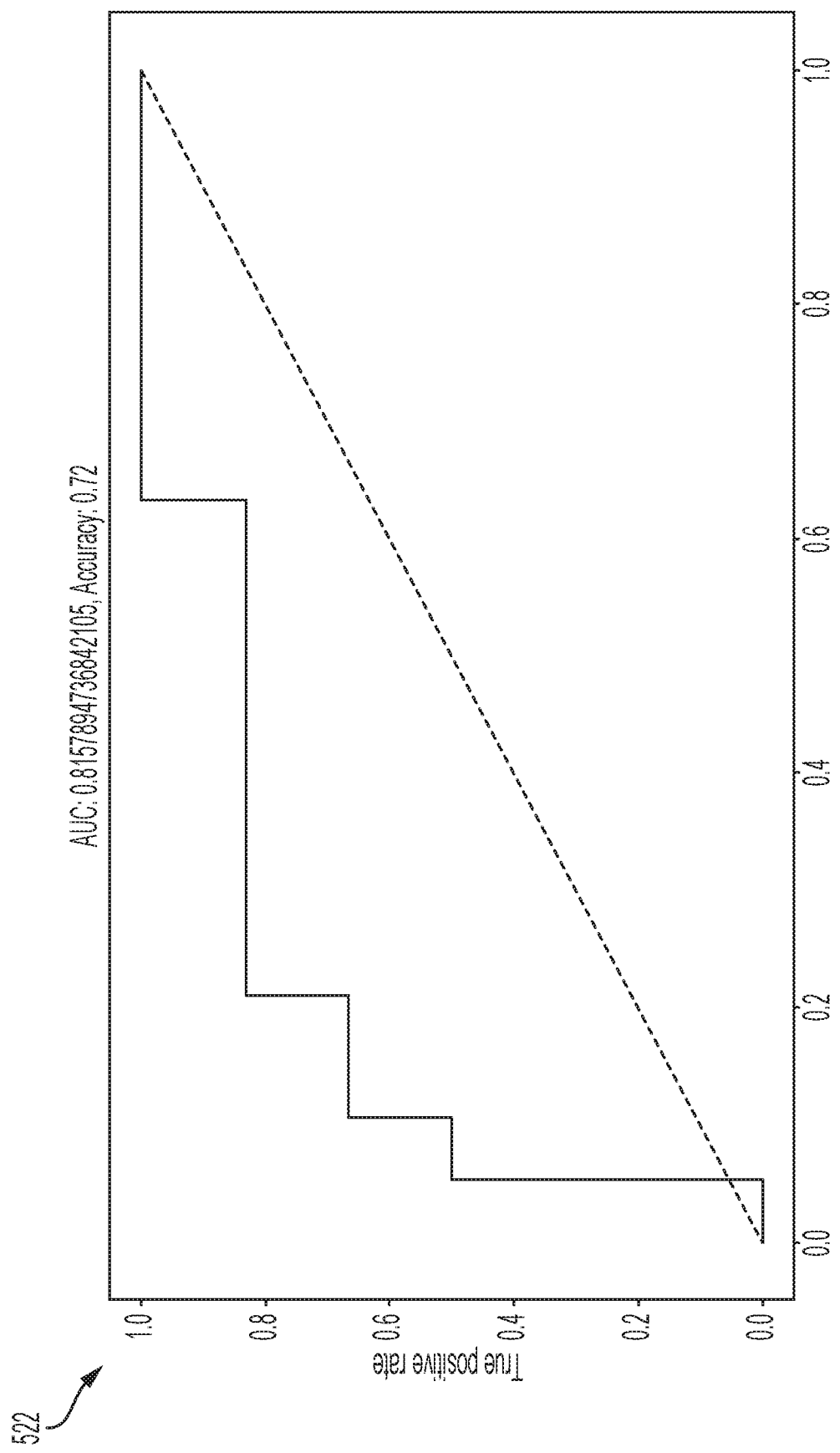
FIG. 5B is another graph of a receiver operating characteristic (ROC) curve for a binary classification of prostate cancer metastases using a machine learning module that takes prostate volume intensities as input.

FIG. 5A and FIG. 5B show receiver operating characteristic (ROC) curves obtained by varying the discrimination threshold and comparing the classification result with the known ground truth from the clinical data. FIG. 5A shows an ROC curve 502 obtained for a 5-fold cross-validation and sample size of 63. An Area Under the Curve (AUC) of 0.81 was obtained for this ROC curve 502. FIG. 5B shows an ROC curve 522 obtained using a wholly distinct test data set (sample size of 25). An AUC of 0.82 was obtained for this ROC curve 522.

A predictive model that did not use machine learning-based analysis of image intensities, and instead utilized a regression model based on clinical variables was evaluated for comparison. The regression model utilized the following clinical variables: patient age, PSA, clinical T stage, Gleason score, and % positive core. PSA refers to a result of a blood test that measures the presence of prostate-specific antigen in a patient. PSA is elevated in the vast majority of patients with prostate cancer (but also in many patients without prostate cancer which is a common pitfall of this test). Clinical T stage refers to a standardized code for reporting the progression of prostate cancer. Clinical T stage may also be referred to as TNM staging for Tumor, Nodule, Metastasis. TNM staging is described in further detail at https://www.cancer.gov/about-cancer/diagnosis-staging/staging. Gleason score refers to the standard Gleason score, and % positive core refers to a value representing a proportion of a plurality of samples collected via biopsy that were identified (e.g., by a pathologist) as positive for prostate cancer.

Figure 5C:
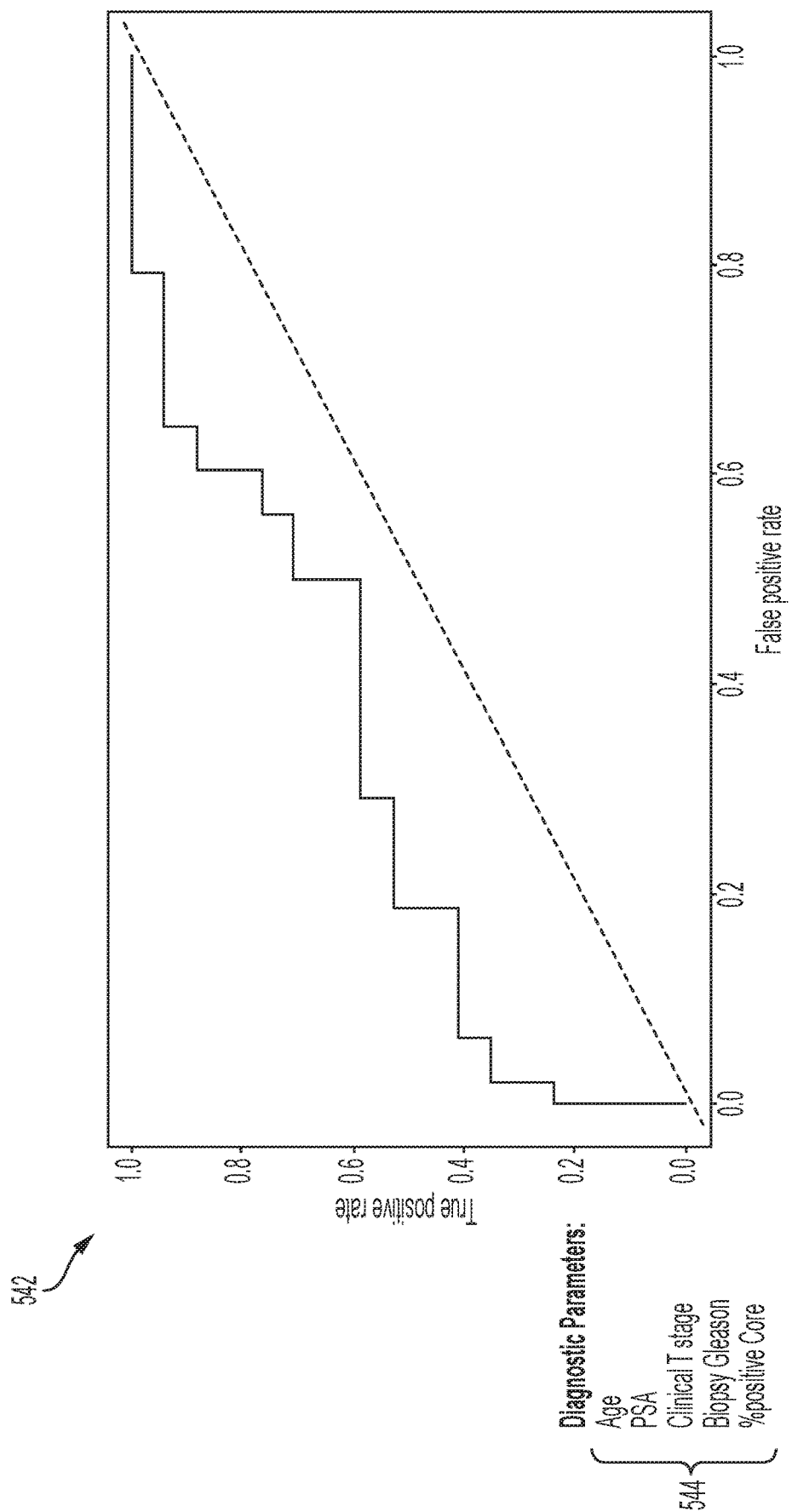
FIG. 5C is a graph of an ROC curve for binary classification of prostate cancer metastasis using a regression model based on clinical variables.

FIG. 5C shows the ROC curve 542 for the regression model (based solely on clinical variables). Notably, the AUC of 0.73 is not as high as the AI-based approach (AUCs of 0.81 and 0.82 as shown in FIGS. 5A and 5B and described herein), indicating higher performance of the AI approach.

Figure 6:
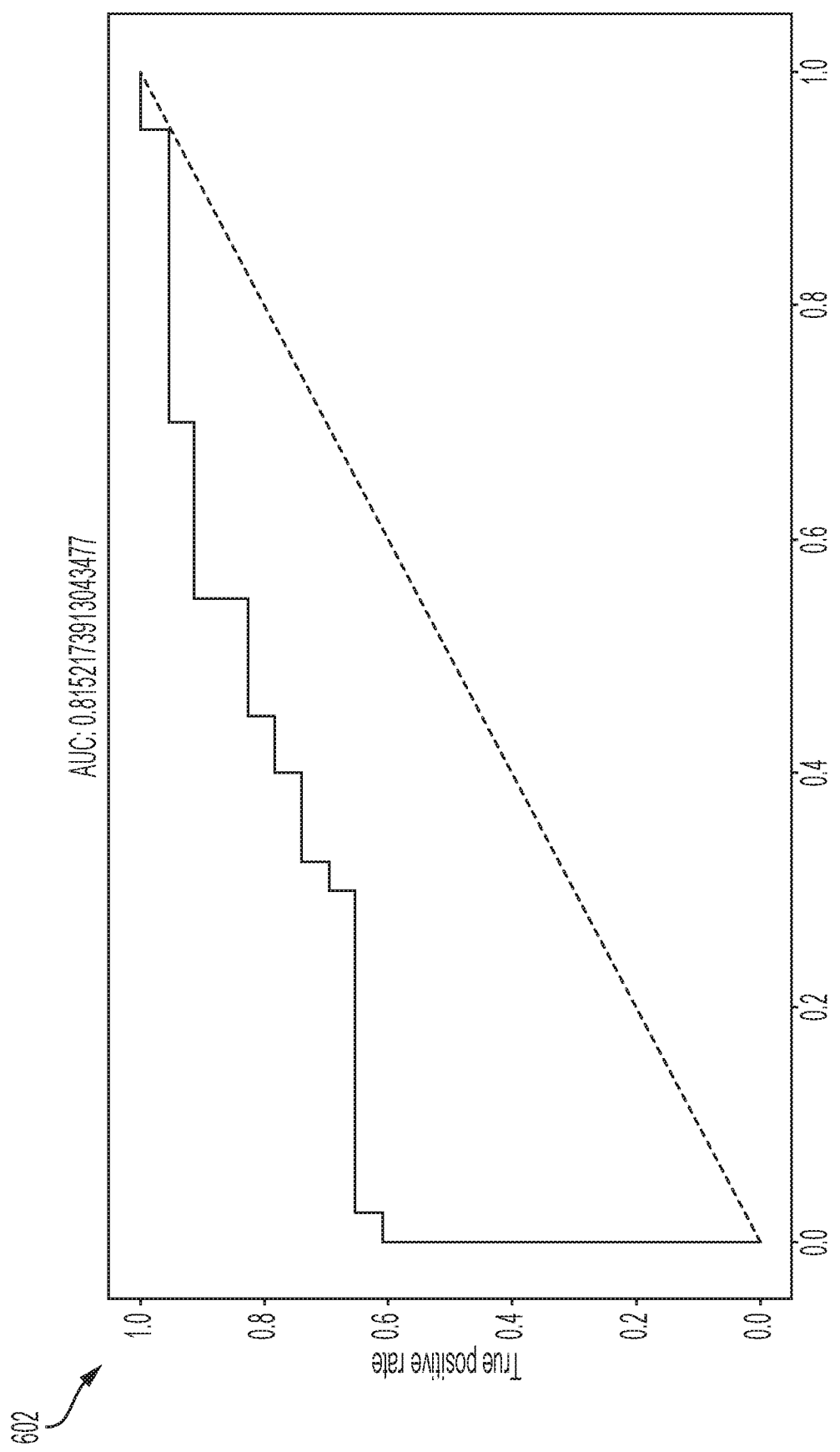
FIG. 6 is a graph of an ROC curve for binary classification of prostate cancer metastases using a machine learning module that takes prostate volume intensities and clinical variables as input.

The second machine learning prediction module, which used both prostate volume intensities and clinical variables was also evaluated. The particular clinical variables used as inputs to the second prediction module were PSA, clinical T stage, Gleason score, and % positive core, as well as a race/ethnicity value. FIG. 6 shows an ROC graph 602 obtained using the second machine learning module. An AUC of 0.82 was obtained.

Accordingly, AI-based analysis of intensity patterns in prostate volumes identified within 3D functional images, via the systems and methods described herein, can be used to assess prostate cancer status in a patient. While the examples described herein demonstrate a binary classification of whether or not a patient has metastases, other prostate cancer status classifications, such as state of current disease, a risk of recurrence, survival prognosis, and the like, may also be determined.

Figure 7:
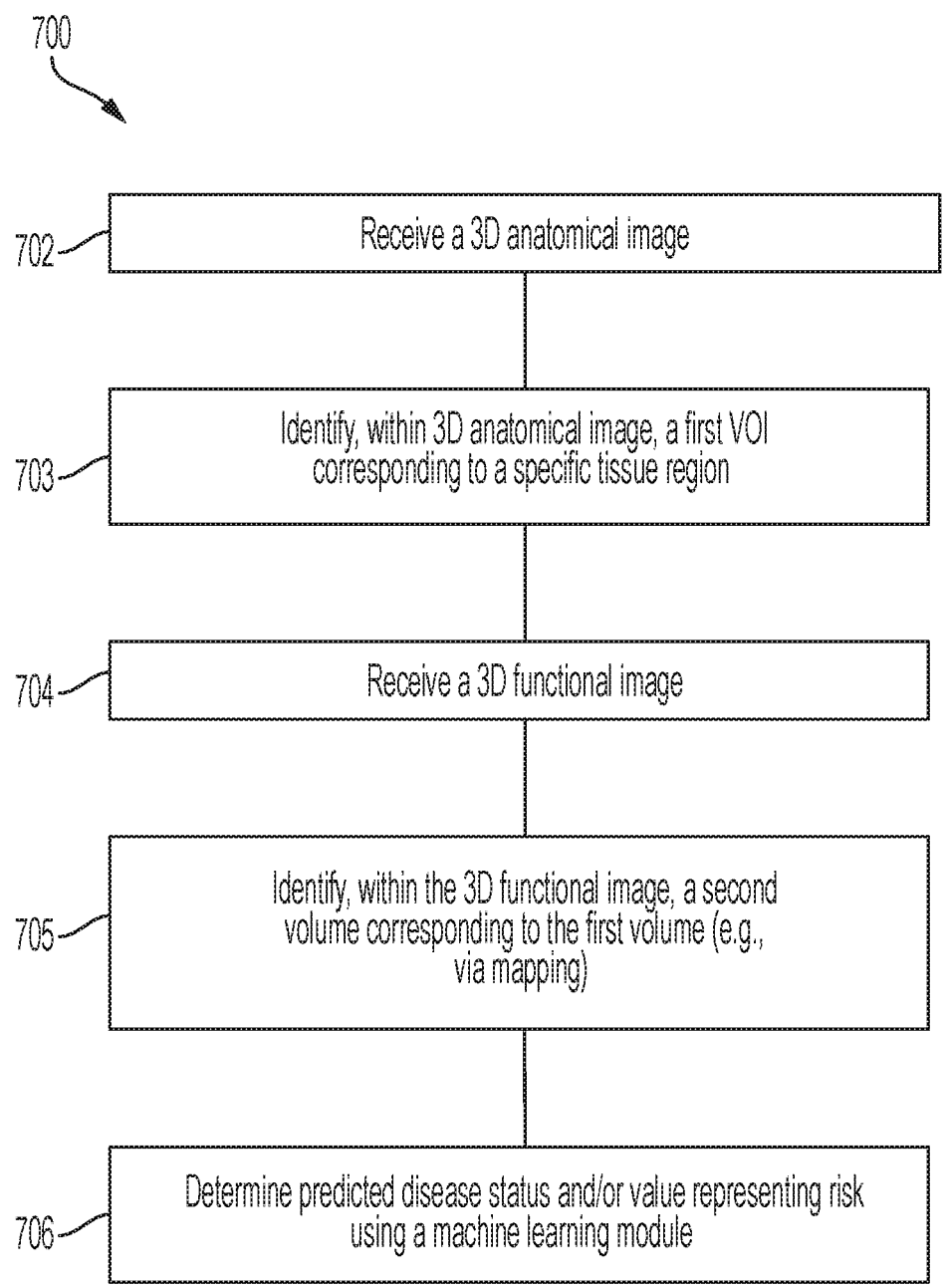
FIG. 7 is a block flow diagram of a process for determining a prostate cancer status of a subject using the AI-based approaches described herein, according to an illustrative embodiment

In particular, FIG. 7 is a block flow diagram of an example process 700 for determining a predicted disease status and/or a value representing risk of the predicted disease status in accordance with the AI-based image analysis approaches described herein. In a first step, a processor receives a 3D anatomical image 702. The processor identifies (e.g., via segmentation) a first volume corresponding to a specific tissue region of interest within the 3D anatomical image 703. The specific region of interest may be a prostate, a brain, a lung, a liver, a stomach, a colon, a breast, etc. The processor receives a 3D functional image 704, such as a PET image or a SPECT image. The processor identifies 705, within the 3D functional image, a second volume corresponding to the first volume (e.g., via mapping). The processor then determines the predicted disease status and/or value representing risk using a machine learning module that receives, as input, (i) intensities of voxels within the 3D functional image that correspond to the first volume (e.g., that lie within the second volume), as well as (ii) one or more clinical variables such as those described herein.

B. Computer System and Network Environment

Figure 8:
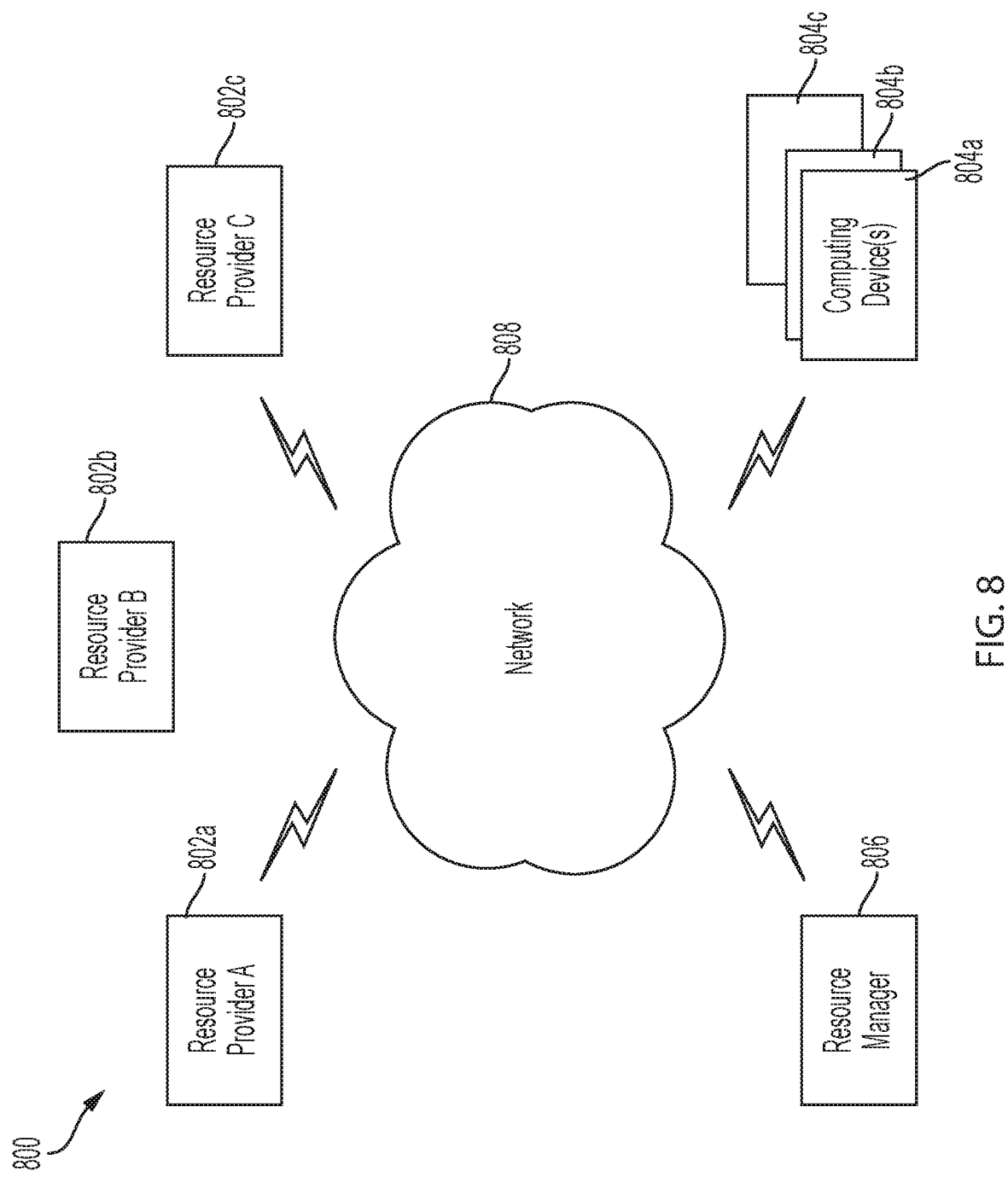
FIG. 8 is a block diagram of an exemplary cloud computing environment, used in certain embodiments.

As shown in FIG. 8, an implementation of a network environment 800 for use in providing systems and methods described herein is shown and described. In brief overview, referring now to FIG. 8, a block diagram of an exemplary cloud computing environment 800 is shown and described. The cloud computing environment 800 may include one or more resource providers 802a, 802b, 802c (collectively, 802). Each resource provider 802 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 802 may be connected to any other resource provider 802 in the cloud computing environment 800. In some implementations, the resource providers 802 may be connected over a computer network 808. Each resource provider 802 may be connected to one or more computing device 804a, 804b, 804c (collectively, 804), over the computer network 808.

The cloud computing environment 800 may include a resource manager 806. The resource manager 806 may be connected to the resource providers 802 and the computing devices 804 over the computer network 808. In some implementations, the resource manager 806 may facilitate the provision of computing resources by one or more resource providers 802 to one or more computing devices 804. The resource manager 806 may receive a request for a computing resource from a particular computing device 804. The resource manager 806 may identify one or more resource providers 802 capable of providing the computing resource requested by the computing device 804. The resource manager 806 may select a resource provider 802 to provide the computing resource. The resource manager 806 may facilitate a connection between the resource provider 802 and a particular computing device 804. In some implementations, the resource manager 806 may establish a connection between a particular resource provider 802 and a particular computing device 804. In some implementations, the resource manager 806 may redirect a particular computing device 804 to a particular resource provider 802 with the requested computing resource.

Figure 9:
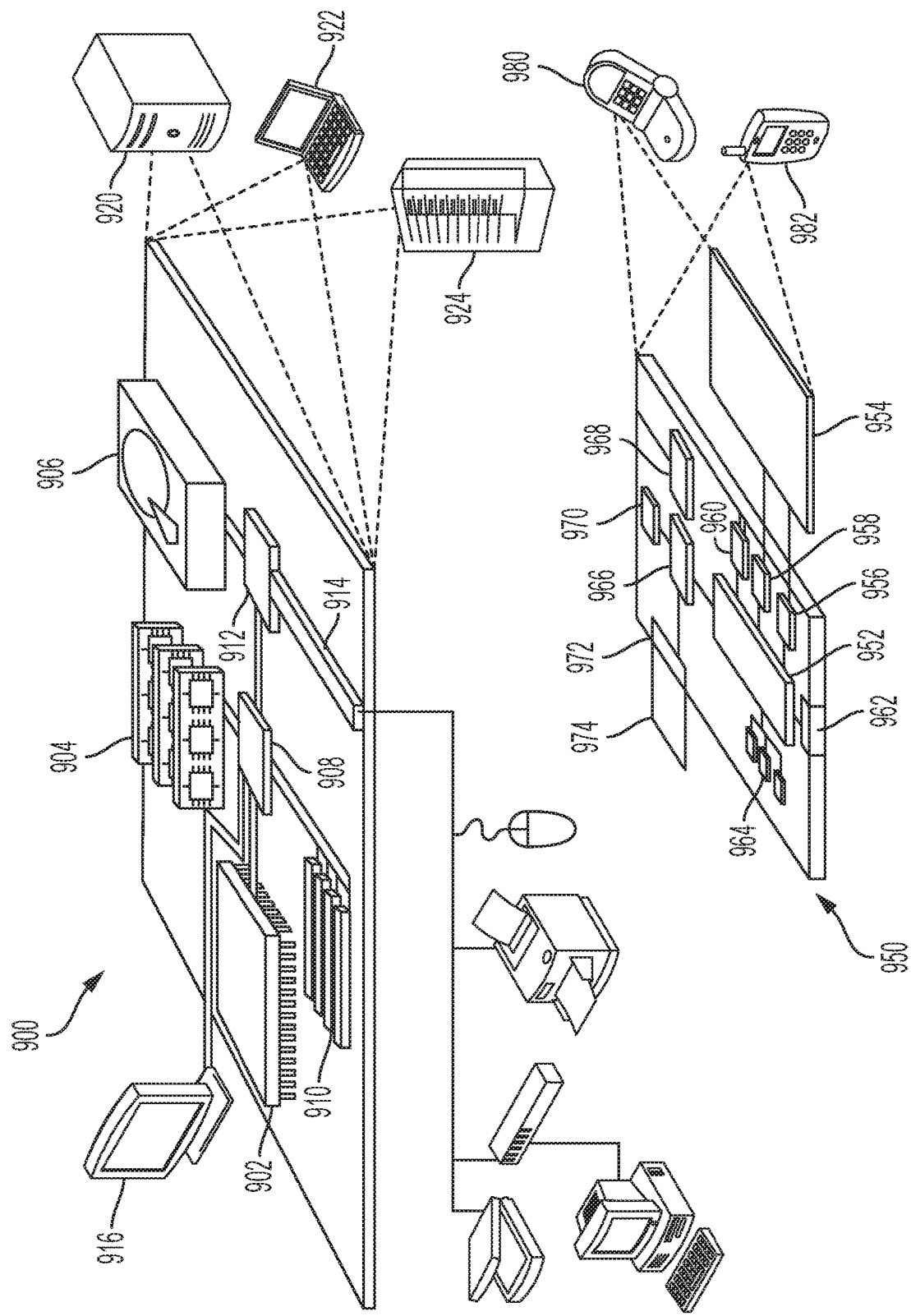
FIG. 9 is a block diagram of an example computing device and an example mobile computing device used in certain embodiments.

FIG. 9 shows an example of a computing device 900 and a mobile computing device 950 that can be used to implement the techniques described in this disclosure. The computing device 900 is intended to represent various forms of digital computers, such as laptops, desktops, workstations, personal digital assistants, servers, blade servers, mainframes, and other appropriate computers. The mobile computing device 950 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 900 includes a processor 902, a memory 904, a storage device 906, a high-speed interface 908 connecting to the memory 904 and multiple high-speed expansion ports 910, and a low-speed interface 912 connecting to a low-speed expansion port 914 and the storage device 906. Each of the processor 902, the memory 904, the storage device 906, the high-speed interface 908, the high-speed expansion ports 910, and the low-speed interface 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as a display 916 coupled to the high-speed interface 908. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 904 stores information within the computing device 900. In some implementations, the memory 904 is a volatile memory unit or units. In some implementations, the memory 904 is a non-volatile memory unit or units. The memory 904 may also be another form of computer-readable medium, such as a magnetic or optical disk.

The storage device 906 is capable of providing mass storage for the computing device 900. In some implementations, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 902), perform one or more methods, such as those described above. The instructions can also be stored by one or more storage devices such as computer- or machine-readable mediums (for example, the memory 904, the storage device 906, or memory on the processor 902).

The high-speed interface 908 manages bandwidth-intensive operations for the computing device 900, while the low-speed interface 912 manages lower bandwidth-intensive operations. Such allocation of functions is an example only. In some implementations, the high-speed interface 908 is coupled to the memory 904, the display 916 (e.g., through a graphics processor or accelerator), and to the high-speed expansion ports 910, which may accept various expansion cards (not shown). In the implementation, the low-speed interface 912 is coupled to the storage device 906 and the low-speed expansion port 914. The low-speed expansion port 914, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. In addition, it may be implemented in a personal computer such as a laptop computer 922. It may also be implemented as part of a rack server system 924. Alternatively, components from the computing device 900 may be combined with other components in a mobile device (not shown), such as a mobile computing device 950. Each of such devices may contain one or more of the computing device 900 and the mobile computing device 950, and an entire system may be made up of multiple computing devices communicating with each other.

The mobile computing device 950 includes a processor 952, a memory 964, an input/output device such as a display 954, a communication interface 966, and a transceiver 968, among other components. The mobile computing device 950 may also be provided with a storage device, such as a micro-drive or other device, to provide additional storage. Each of the processor 952, the memory 964, the display 954, the communication interface 966, and the transceiver 968, are interconnected using various buses, and several of the components may be mounted on a common motherboard or in other manners as appropriate.

The processor 952 can execute instructions within the mobile computing device 950, including instructions stored in the memory 964. The processor 952 may be implemented as a chipset of chips that include separate and multiple analog and digital processors. The processor 952 may provide, for example, for coordination of the other components of the mobile computing device 950, such as control of user interfaces, applications run by the mobile computing device 950, and wireless communication by the mobile computing device 950.

The processor 952 may communicate with a user through a control interface 958 and a display interface 956 coupled to the display 954. The display 954 may be, for example, a TFT (Thin-Film-Transistor Liquid Crystal Display) display or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may provide communication with the processor 952, so as to enable near area communication of the mobile computing device 950 with other devices. The external interface 962 may provide, for example, for wired communication in some implementations, or for wireless communication in other implementations, and multiple interfaces may also be used.

The memory 964 stores information within the mobile computing device 950. The memory 964 can be implemented as one or more of a computer-readable medium or media, a volatile memory unit or units, or a non-volatile memory unit or units. An expansion memory 974 may also be provided and connected to the mobile computing device 950 through an expansion interface 972, which may include, for example, a SIMM (Single In Line Memory Module) card interface. The expansion memory 974 may provide extra storage space for the mobile computing device 950, or may also store applications or other information for the mobile computing device 950. Specifically, the expansion memory 974 may include instructions to carry out or supplement the processes described above, and may include secure information also. Thus, for example, the expansion memory 974 may be provide as a security module for the mobile computing device 950, and may be programmed with instructions that permit secure use of the mobile computing device 950. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 952), perform one or more methods, such as those described above. The instructions can also be stored by one or more storage devices, such as one or more computer- or machine-readable mediums (for example, the memory 964, the expansion memory 974, or memory on the processor 952). In some implementations, the instructions can be received in a propagated signal, for example, over the transceiver 968 or the external interface 962.

The mobile computing device 950 may communicate wirelessly through the communication interface 966, which may include digital signal processing circuitry where necessary. The communication interface 966 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 968 using a radio-frequency. In addition, short-range communication may occur, such as using a Bluetooth®, Wi-Fi™, or other such transceiver (not shown). In addition, a GPS (Global Positioning System) receiver module 970 may provide additional navigation- and location-related wireless data to the mobile computing device 950, which may be used as appropriate by applications running on the mobile computing device 950.

The mobile computing device 950 may also communicate audibly using an audio codec 960, which may receive spoken information from a user and convert it to usable digital information. The audio codec 960 may likewise generate audible sound for a user, such as through a speaker, e.g., in a handset of the mobile computing device 950. Such sound may include sound from voice telephone calls, may include recorded sound (e.g., voice messages, music files, etc.) and may also include sound generated by applications operating on the mobile computing device 950.

The mobile computing device 950 may be implemented in a number of different forms, as shown in the figure. For example, it may be implemented as a cellular telephone 980. It may also be implemented as part of a smart-phone 982, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for determining a predicted disease status and/or a value corresponding to predicted risk of the disease status based on automated analysis of intensities of a three-dimensional (3D) functional image, the method comprising:
    (a) receiving, by a processor of a computing device, a 3D anatomical image of a subject obtained using an anatomical imaging modality, wherein the 3D anatomical image comprises a graphical representation of tissue within the subject;
    (b) identifying, by the processor, within the 3D anatomical image, a target volume of interest (VOI) corresponding to a prostate region of the subject;
    (c) receiving, by the processor, a 3D functional image of the subject obtained using a functional imaging modality; and
    (d) determining, by the processor, a predicted disease status of the subject and/or a value corresponding to predicted risk of the disease status of the subject using a machine learning module that (i) receives, as input, intensities of only those voxels of the 3D functional image identified as corresponding to the target VOI of the anatomical image and (ii) does not receive, as input, intensities of other voxels of the 3D functional image.

2. The method of claim 1, wherein the method comprises identifying the voxels of the 3D functional image corresponding to the target VOI of the anatomical image by:
    identifying, by the processor, within the 3D functional image, a 3D prostate volume corresponding to the target VOI identified within the 3D anatomical image and identifying voxels of the 3D functional image lying within the 3D prostate volume as corresponding to the target VOI of the anatomical image.

3. The method of claim 1, wherein the machine learning module receives, as input, only intensities of the voxels of the 3D functional image identified as corresponding to the target VOI of the anatomical image.

4. The method of claim 1, wherein the machine learning module further receives, as input, one or more clinical variables.

5. The method of claim 4, wherein the one or more clinical variables comprise one or more members selected from the group consisting of:
 a race/ethnicity;
 a prostate specific antigen (PSA) level and/or velocity;
 a hemoglobin level;
 a lactate dehydrogenase level;
 an albumin level;
 a clinical T stage;
 a biopsy Gleason score; and
 a percentage positive core score.

6. The method of claim 1, comprising determining the predicted disease status, wherein the predicted disease status is a classification corresponding to a prediction of aggressive disease status.

7. The method of claim 6, wherein the classification comprises one or more of the following classes corresponding to predictions of whether the subject has and/or likely will develop one or more metastases:
 an overall metastases class, wherein assignment to the overall metastases class corresponds to a prediction that the subject has and/or will likely develop one or more metastases;
 one or more particular metastases class, each corresponding to a particular type of metastases wherein assignment to the particular metastases class corresponds to a prediction that the subject has and/or will likely develop the particular type of metastases; and
 a no metastases class, wherein assignment to the no metastases class corresponds to a prediction that the subject had not and/or is not likely to develop one or more metastases.

8. The method of claim 6, wherein the machine learning module generates, as output, one or more likelihood values representing likelihood(s) of overall metastases and/or one or more particular types of metastases, and wherein determining the classification comprises comparing the one or more likelihood values with one or more thresholds.

9. The method of claim 1, wherein the method comprises determining the value corresponding to predicted risk of the disease status of the subject, and wherein the disease status is an aggressive disease status.

10. The method of claim 9, wherein the value represents a likelihood that the subject has and/or will develop one or more metastases.

11. The method of claim 10, wherein the value represents a likelihood that the subject has and/or will develop one or more of a particular type of metastases.

12. The method of claim 9, comprising determining a plurality of values, each corresponding to a particular type of metastases and representing a likelihood that the subject has and/or will develop one or more of the particular type of metastases.

13. The method of claim 1, wherein the disease is prostate cancer.

14. The method of claim 1, wherein the machine learning module comprises a convolutional neural network (CNN).

15. The method of claim 1, wherein the anatomical image is a CT scan.

16. The method of claim 1, wherein the functional image is a PET image obtained following administration of a radiopharmaceutical to the subject.

17. The method of claim 16, wherein the radiopharmaceutical comprises a prostate specific membrane antigen (PSMA) binding agent.

18. The method of claim 17, wherein the PSMA binding agent is [18F]DCFPyL.

19. The method of claim 1, wherein the functional image is a SPECT image.

20. A system for determining a predicted disease status and/or a value corresponding to predicted risk of the disease status based on automated analysis of intensities of a three-dimensional (3D) functional image, the system comprising:
 a processor of a computing device; and
 a memory having instructions stored thereon, wherein the instructions, when executed by the processor, cause the processor to:
  (a) receive a 3D anatomical image of a subject obtained using an anatomical imaging modality, wherein the 3D anatomical image comprises a graphical representation of tissue within the subject;
  (b) identify, within the 3D anatomical image, a target volume of interest (VOI) corresponding to a prostate region of the subject;
  (c) receive a 3D functional image of the subject obtained using a functional imaging modality; and
  (d) determine a predicted disease status of the subject and/or a value corresponding to predicted risk of the disease status of the subject using a machine learning module that (i) receives, as input, intensities of only those voxels of the 3D functional identified as corresponding to the target VOI of the anatomical image and (ii) does not receive, as input, intensities of other voxels of the 3D functional image.

* * * * *